(12) United States Patent
Miguéns Pereira et al.

(10) Patent No.: US 12,410,178 B2
(45) Date of Patent: Sep. 9, 2025

(54) SMALL CATIONIC ORTHO-5,15-DI-HETEROARYL-PORPHYRIN DERIVATIVES AND THEIR APPLICATIONS IN PHOTOINACTIVATION OF MICROORGANISMS

(71) Applicant: UNIVERSIDADE DE COIMBRA, Coimbra (PT)

(72) Inventors: Maria Miguéns Pereira, Coimbra (PT); Gabriela Conceição Duarte Jorge Da Silva, Coimbra (PT); Luís Guilerme Da Silva Arnaut Moreira, Coimbra (PT); Carolina Dos Santos Vinagreiro, Coimbra (PT); Kate Cristina Blanco, Sao Carlos (PT); Vanderiei Salvador Bagnato, Sao Carlos (PT); Natalia Mayumi Inada, Sao Carlos (PT)

(73) Assignee: UNIVERSIDADE DE COIMBRA, Coimbra (PT)

(*) Notice: Subject to any disclaimer, the term of this patent is extended or adjusted under 35 U.S.C. 154(b) by 914 days.

(21) Appl. No.: 17/618,971

(22) PCT Filed: Jun. 15, 2020

(86) PCT No.: PCT/IB2020/055584
§ 371 (c)(1),
(2) Date: Dec. 14, 2021

(87) PCT Pub. No.: WO2020/250207
PCT Pub. Date: Dec. 17, 2020

(65) Prior Publication Data
US 2022/0372043 A1   Nov. 24, 2022

(30) Foreign Application Priority Data
Jun. 14, 2019 (PT) ........................ 115581

(51) Int. Cl.
*C07D 487/22* (2006.01)
*A61K 31/555* (2006.01)
*A61K 41/00* (2020.01)
*A61K 45/06* (2006.01)
*A61P 31/04* (2006.01)

(52) U.S. Cl.
CPC .......... *C07D 487/22* (2013.01); *A61K 31/555* (2013.01); *A61K 41/0057* (2013.01); *A61K 45/06* (2013.01); *A61P 31/04* (2018.01)

(58) Field of Classification Search
None
See application file for complete search history.

(56) References Cited

FOREIGN PATENT DOCUMENTS

WO          00/43395 A2      7/2000
WO          2006053707 A1    5/2006

OTHER PUBLICATIONS

Bejune et al: "New Dicationic Porphyrin Ligands Suited for Intercalation into B-Form DNA", Inorganic Chemistry, vol. 42, No. 25, Dec. 1, 2003 (Dec. 1, 2003), pp. 8465-8475 (Year: 2003).*
Hamblin et al. "Inorganic Salts and Antimicrobial Photodynamic Therapy: Mechanistic Conundrums?" Molecules 2018, 23, 3190 (Year: 2018).*
Yamamoto et al: "Interaction of Dicationic Bis(imidazoliumyl)porphyrinatometals with DNA", Bulletin of the Chemical Society of Japan, vol. 76, No. 10, Oct. 1, 2003 (Oct. 1, 2003), pp. 1947-1955 (Year: 2003).*
Zhu et al. "Comparison between porphin, chlorin and bacteriochlorin derivatives for photodynamic therapy: Synthesis, photophysical properties, and biological activity" European Journal of Medicinal Chemistry 160 (2018) 146-156 (Year: 2018).*
Tomoko Yamamoto et al: "Interaction of Dicationic Bis(imidazoliumyl)porphyrinatometals with DNA", Bulletin of Chemical Society of Japan, vol. 76, No. 10, (Oct. 1, 2003) pp. 1947-1955, XP055743180, JP, ISSN: 0009-2673, DOI: 10.1246/bcsj.76.1947.
International Search Report of PCT/IB2020/055584 Mailed on Nov. 6, 2020.

* cited by examiner

*Primary Examiner* — Adam C Milligan
*Assistant Examiner* — Jed A Kucharczk
(74) *Attorney, Agent, or Firm* — Rivka Friedman

(57) ABSTRACT

The present invention relates to small cationic ortho-5,15-di-heteroaryl porphyrin derivatives, in particular porphyrins, chlorins or bacteriochlorin of formula (I) or pharmaceutically acceptable salts thereof.
This invention also relates to the use of the above-mentioned cationic ortho-5,10-di-heteroaryl porphyrin derivatives of Formula (I) or a pharmaceutically acceptable salts thereof, in photodynamic inactivation of microorganisms, where the referred derivatives are able to treat the same in the presence of an adequate light.
The present invention also describes pharmaceutical compositions comprising one or more of the cationic ortho-5, 10-di-heteroaryl porphyrin derivatives, in particular prophyrins, chlorins or bacteriochlorins of Formula (I), or pharmaceutically acceptable salts thereof, for the treatment of bacterial and/or fungi and/or yeasts and/or viral infections, in humans or animals.

12 Claims, 12 Drawing Sheets

Formula (I)

Formula (Ia)

Formula (Ib)

Formula (Ic)

SMALL CATIONIC ORTHO-5,15-DI-HETEROARYL-PORPHYRIN DERIVATIVES AND THEIR APPLICATIONS IN PHOTOINACTIVATION OF MICROORGANISMS

TECHNICAL FIELD

The present application relates to new cationic ortho-5,15-di-heteroaryl porphyrin derivatives of small size, namely porphyrins, chlorins or bacteriochlorin of Formula (I), and their preparation process and their use in photodynamic inactivation (PDI) of microorganisms.

BACKGROUND OF THE INVENTION

Emergence of resistance to antibiotics in pathogenic bacteria has become a significant public health concern. Deaths attributable to antimicrobial resistance are expected to reach 10 million annually worldwide by 2050, and place a tremendous burden in healthcare systems. The major challenges to overcome are resistance originated by multidrug-resistant Gram-negative bacteria and by bacteria in biofilms. Gram-positive bacteria have their cytoplasmic membrane surrounded by a relatively porous layer of peptidoglycan and lipoteichoic acid that allows for the diffusion of macromolecules with molecular weight in the 30,000-60,000 Da range. However, Gram-negative bacteria have cell envelopes composed of an inner cytoplasmic membrane and an outer membrane separated by a peptidoglycan-containing periplasm. This outer membrane forms a physical and functional barrier between the cell and its environment that limits the uptake to relatively hydrophilic compounds with a molecular weight lower than 700 Da which can diffuse through the porin channels (1). Bacterial infections involving bacterial biofilms are very difficult to eradicate because biofilms protect bacteria from hostile environments. Various mechanism contribute to the resistance of bacterial biofilms, namely decreased diffusion of biocides, deactivation of the antimicrobial agent by outer layers of the biofilm, dormancy of the bacteria in some regions of the biofilm, and differentiation into a highly protected phenotypic state, in addition to conventional resistance mechanisms such as drug pumps.

Photodynamic inactivation (PDI) of microorganisms is a clinically approved treatment based on the administration of a photosensitizing molecule, its accumulation in the microorganism, and after some time, illumination with light absorbed by the photosensitizer (2). The absorption of light leaves the photosensitizer in an electronically excited state that reacts with substrate molecules by electron transfer reactions with the formation of superoxide anion and hydroxyl radicals (type I reaction), or transfers its electronic energy to ground-state molecular oxygen generating singlet oxygen (type II reaction). These photogenerated reactive oxygen species (ROS) trigger biological mechanisms that eventually lead to the death of the microorganism and make PDI an effective disinfection and/or antiseptic and/or antibiotic procedure.

Herein, the term "microorganism" covers species such as bacteria, fungi, yeasts, viruses or protozoa (e.g., *Plasmodium falciparum*, responsible for malaria, *Trypanosoma cruzi*, responsible for Chagas' disease, *Entamoeba histolytica*, responsible for amoebiasis). Herein, the term "biofilm" refers to aggregates of microorganisms in a matrix of their own synthesis when attached to a solid surface.

Herein, the term "multidrug-resistant" denotes microorganisms resistant to one key antimicrobial agent, including methicillin resistance in *S. aureus* (i.e. MRSA), because such microorganisms often demonstrate cross or co-resistance to multiple cases of antimicrobials.

Meso-substituted cationic porphyrins such as meso-tetra (N-methyl-4-pyridyl)porphyrin meso-tetra(4-N,N,N-trimethylanilinium)porphyrin were shown to inactivate Gram-negative bacteria (3), and the same was shown for a cationic zinc pyridinium phthalocyanine (4). These pioneer studies helped to realize that effective PDI of Gram-positive bacteria requires a photosensitizer with a pronounced cationic charge and various polycationic photosensitizer conjugates have been prepared and tested (5). Progress along these lines led to cationic tetrapyridyl porphyrins (1), to polycationic lysine conjugates of chlorin e6 (5) and to bacteriochlorins with quaternized ammonium groups (6) that can reduce the survival of bacteria by 4 to 6 log units when used in micromolar concentrations and combined with light doses of tens of joules per square centimeter, $J/cm^2$. It became accepted in the field that PDI of Gram-negative bacteria required as many cationic charges as possible on a nominally hydrophobic tetrapyrrole photosensitizer (7).

Although PDI of bacteria suspensions by 5-6 orders of magnitude using micromolar photosensitizer concentrations and light doses ca. 10 $J/cm^2$ was achieved (7) the transfer of such photosensitizers to clinical applications has been mostly unsuccessful. A recent review of the patent landscape of PDI of microorganisms shows that innovative methods and devices have been disclosed but the clinical options for molecular photosensitizers are very limited and inexistent for the case of biofilms (8).

Attempts to improve the efficacy of antimicrobial agents include the combination of photosensitizers for PDI with small molecules and with antimicrobial peptides. Small molecular species that potentiate photoinactivation of microorganisms include but not limited to: (i) small molecule inhibitors of pathogen efflux systems (9), (ii) small polycationic molecular species that competitively displace the native divalent cations $Ca^{+2}$ and $Mg^{2+}$ that exert a stabilizing effect on the lipopolysaccharides of the outer membrane of microorganism and disrupt this membrane (10), (iii) species such as azide and inorganic salts that undergo electron transfer to the photosensitizer triplet state to generate reactive radicals that potentiate PI of microorganisms (11). Antimicrobial peptides with positive charge and proper hydrophobic moiety may damage bacteria outer membranes by pore-forming and nonpore-forming mechanisms and have been delivered together with photosensitizers to increase the potency of photosensitizers (12).

A likely reason for the failure to translate PDI of (planktonic) single-cell bacteria suspensions to clinical settings is the fact that many of the infections plaguing humans are actually caused by bacteria in the biofilm mode of growth and not in the planktonic form. This is especially relevant for PDI because this treatment modality is expected to address medical needs in hard to treat localized infections. The basic premise in that the photosensitizer should be capable of local, topical or intracavital administration into the infected area, followed, after a suitable time, by delivery of the appropriate dose of the optimum wavelength of light into the infected area by means of fiber optic, diffusing tip, fiber bundle, implantable light source, or direct illumination of a surgical exposed area (2). Possible clinical applications include, but are not limited to, oral candidiasis, periodontal diseases, wound infections including burn wound infections and surgical wound infections, herpes, acne, onychomycosis, papillomatosis, removal of residual infection of abscess sites after surgical drainage, sinusitis, urinary tract infections and corneal infections.

In order to succeed in PDI of localized infections where biofilms are present, the design of the photosensitizers must take into consideration both the challenges of Gram-positive and Gram-negative bacteria and the challenges of biofilms. This invention discloses, for the first time, photosensitizers that are very efficient in PDI of microorganism both in planktonic and in biofilm forms. It has not been appreciated in earlier uses of photosensitizers for PDI that a very large number of positive charges increases hydrophilicity and reduces the partition to bacteria cell walls and biofilms. Furthermore, earlier uses of photosensitizers for PDI did not explore the dependence of bacteria cell uptake and biofilm penetration on the size of the photosensitizers. For example, photosensitizers of Formula (I) can have molecular weights as low as 470 Da while having 2 positive charges. Photosensitizers of Formula (I) solve the technical problem of having small cationic molecular species with high molar absorption coefficients, which allows them to be taken up by microorganism, including Gram-negative bacteria, and to diffuse rapidly in the biofilms, to enable the photoactivation of the microorganisms at photosensitizer doses lower than 1 mg per liter (1 mg/L).

It is an essential feature of this invention the disclosure of photosensitizers where the distribution of the positive charges is especially designed to maximize electrostatic interactions with cytoplasmic and outer membranes of bacteria. It was not realized before that the distribution of positive charges to atoms on the upper and/or lower sides of the macrocycle, that are more exposed to the surrounding medium of the photosensitizer molecular species, enables electrostatic interactions that are effective for a lower total positive charge of the photosensitizer. This allows for the use of small cationic porphyrin derivatives that combine the small size required for penetration in bacteria and diffusion into biofilms, with the presence of a small number of positive charges. This invention is realized placing at least one nitrogen atom in one ortho position of a heteroaryl group bound to a meso position of a porphyrin derivative, where said nitrogen atom is quaternized. The fact that the said nitrogen atom is in the ortho position of an heteroaryl ring and is bound to a methyl group, produces steric interactions with the macrocycle that force the heteroaryl group to rotate and adopt a nearly orthogonal orientation with respect to the macrocycle. Placed in the ortho position of the orthogonal heteroaryl group, the nitrogen atom directs the methyl group out above or below the macrocycle ring, which maximizes the exposure of the positive charges to the medium. This is illustrated in FIG. 1.

In view of the orientations of the positive charges induced by nitrogen atoms in the two ortho position of a heteroaryl group, imidazoyl groups are preferred heteroaryl groups. They are also preferred for their small size.

Another preferred embodiment of the present invention is the complexation of the porphyrin derivatives in Formula (II) with metal ions such as Mg, Al, Si, Zn, Pd, Ag or In. These metal ions form diamagnetic, closed shell, complexes with porphyrin derivatives. Such metalloporphyrin derivatives are characterized having the highest occupied molecular orbital (HOMO) and the lowest unoccupied molecular orbital (LUMO) very similar to the HOMO and LUMO of the free-base porphyrin derivatives (13). In these circumstances, the photochemistry of the metalloporphyrin is controlled mostly by the internal heavy-atom effect of the metal ion, which accelerates intersystem crossing between singlet and triplet manifolds. The heavy-atom effect increases with the atomic number of the metal. For metals such as Zn, the heavy-atom effect is sufficient to increase intersystem crossing from the lowest excited singlet state to the lowest triplet state and increase the triplet state quantum yield of the photosensitizer to nearly unity, but insufficient to increase the intersystem crossing from the triplet state to the ground state of the photosensitizer and lower its triplet state lifetime below the microsecond range. Given that nearly unit triplet state quantum yields and long triplet lifetimes are prerequisites for efficient interaction between photosensitizer molecules and molecular oxygen, and that the efficiency of ROS generation depends on that interaction, this invention discloses most preferred photosensitizers for PDI of microorganism, including microorganisms in the biofilm mode of growth, with the formula (II)

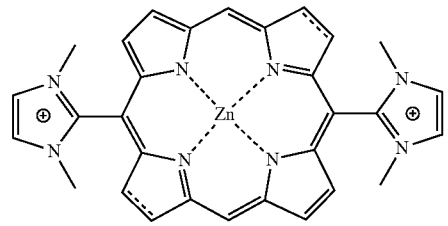

Formula (II)

Wherein ‐‐‐‐‐‐ represents a carbon-carbon single bond or a carbon-carbon double bond. The presence of the metal ion in the center of the macrocycle has a negligible impact on its volume. Hence, the molecular species of Formula (II) can be specifically a porphyrin with the formula (IIa)

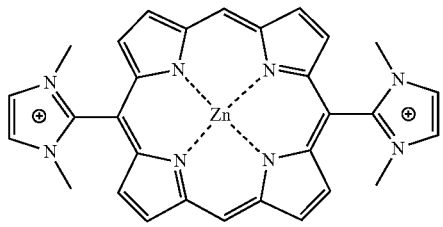

Formula (IIa)

which was represented in FIG. 1 in a different perspective. Identically, the molecular species of Formula (II) can be a bacteriochlorin with the Formula (IIb)

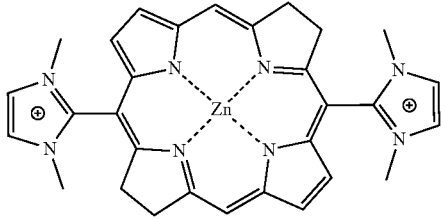

Formula (IIb)

or a chlorin with formula (IIc)

Formula (IIc)

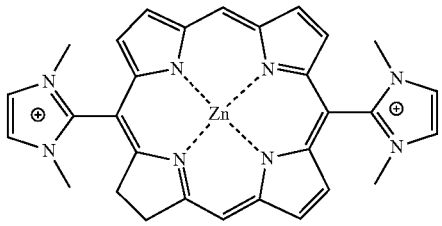

It could not be anticipated by the person skilled in the art that small cationic ortho-5,15-di-heteroaryl porphyrin derivatives of Formula (I) could be very phototoxic towards microorganisms and biofilms, but not phototoxic towards eukaryotic cells. Indeed, the closest prior art is the zinc(II) phenylporphinate of Formula (III), which was shown to be very phototoxic towards human cells in vitro: 50% of human HeLa cells are killed at a concentration of 1.2 µM (14). Such a high phototoxicity towards human cells immediately discourages the use of such compounds to treat infections in the human body. A last example of close prior art is meso-(di-cis[4-N-methyl-pyridyl]cis-diphenyl-porphyrin) of Formula (IV), which was shown to be phototoxic towards flies but not distinctive from other meso-substituted porphyrins in terms of photogeneration of cytotoxic agents (15). These studies with monocationic imidazoyl-substituted meso-porphyrins or with dicationic N-methylpyridyl-substituted meso-porphyrins could not anticipate that dicationic imidazolyl porphyrins would not be phototoxic towards human cells but could be very phototoxic towards microorganism. The key to understand these unexpected differences in phototoxicity is the distribution of charges illustrated in FIG. 1. The large density of positive charge above and below the plane of the macrocycle is a specific property of these molecular species that imparts specificity towards the outer membrane of bacteria. Additionally, the small size favors diffusion in biofilms.

Formula (III)

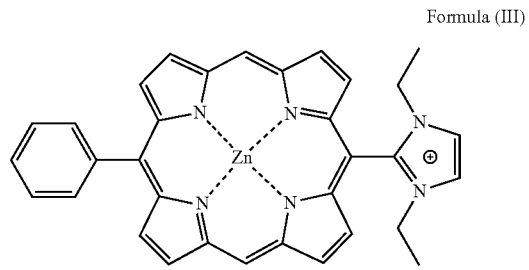

Formula (IV)

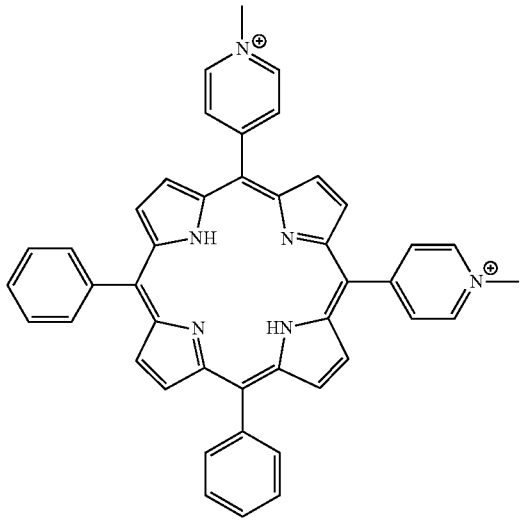

The use of small cationic ortho-5,15-di-heteroaryl porphyrin derivatives of Formula (I) as photosensitizers in the photodynamic inactivation of microorganisms offers various advantages over the state-of-the-art photosensitizers. Indeed, this family of photosensitizers has:
  Intense absorption of light
  High stability and high photostability
  Ability to generate high yields of reactive oxygen species
  Very low toxicity or phototoxicity towards human cells
  High specificity to interact with the outer membranes of microorganisms
  Solubility in biocompatible pharmaceutical vehicles
  Ability to diffuse inside biofilms without being deactivated
  High phototoxicity towards microorganisms, including multidrug resistant Gram-negative bacteria.

These properties can be related to two structural and electronic features of porphyrin derivatives with Formula (I): the small molecular size and the distribution of excess positive charge around the macrocycle.

The present invention also discloses processes to synthesize such photosensitizers and, by the way of examples, illustrates the use of these photosensitizers to inactivate bacteria in planktonic and in biofilm forms.

SUMMARY OF THE INVENTION

The purpose of the present invention is to offer new cationic ortho-5,15-di-heteroaryl porphyrin derivatives of small size, namely porphyrins, chlorins or bacteriochlorin of Formula (I):

Formula (I)

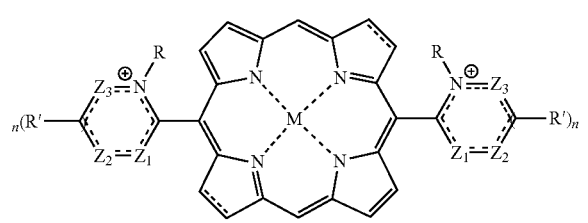

wherein:

~~~~~~ represents a carbon-carbon single bond or a carbon-carbon double bond;

M is $H_2$ or a metal ion selected from Mg, Al, Si, Zn, Pd, Ag, In;

R is chosen from unsubstituted or substituted alkyl, unsubstituted or substituted heteroalkyl, unsubstituted or substituted aryl, unsubstituted or substituted heteroaryl, provided that R has fewer than 12 atoms;

For n=0, then $Z_1$, $Z_2$ and $Z_3$ are each independently chosen from oxygen or from YR", where Y are atoms in the ring each independently chosen from carbon, sulfur or nitrogen, and R" is bonded to Y and each independently chosen from hydrogen or from R;

For n=1, then $Z_1$, $Z_2$ and $Z_3$ are each independently chosen from YR", where Y are atoms in the ring each independently chosen from carbon, sulfur or nitrogen, R" is bonded to Y, and R' and R" are each independently chosen from hydrogen or from R;

or pharmaceutically acceptable salts thereof;

for use in the photodynamic inactivation of pathogenic microorganisms.

Hence, the compounds of Formula (I) may be porphyrins of formula

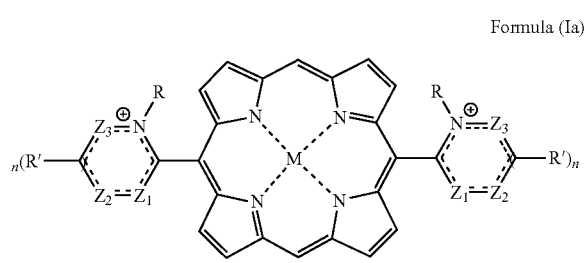

Formula (Ia)

wherein:

~~~~~~ represents a carbon-carbon single bond or a carbon-carbon double bond;

M is $H_2$ or a metal ion selected from Mg, Al, Si, Zn, Pd, Ag, In;

R is chosen from unsubstituted or substituted alkyl, unsubstituted or substituted heteroalkyl, unsubstituted or substituted aryl, unsubstituted or substituted heteroaryl, provided that R has fewer than 12 atoms;

For n=0, then $Z_1$, $Z_2$ and $Z_3$ are each independently chosen from oxygen or from YR", where Y are atoms in the ring each independently chosen from carbon, sulfur or nitrogen, and R" is bonded to Y and each independently chosen from hydrogen or from R;

For n=1, then $Z_1$, $Z_2$ and $Z_3$ are each independently chosen from YR", where Y are atoms in the ring each independently chosen from carbon, sulfur or nitrogen, R" is bonded to Y, and R' and R" are each independently chosen from hydrogen or from R; or pharmaceutically acceptable salts thereof.

Specific preferred compounds of the invention include the small cationic ortho-5,15-di-heteroaryl porphyrin of Formula (Ia) where: M is $Zn^{2+}$, $Z_1$ is nitrogen, $Z_2$ and $Z_3$ are carbon R is methyl, R" is methyl or hydrogen, and n=0 which means that R' is not present in the structure and $Z_2$ is directly bonded to $Z_3$.

Alternatively, the compounds of Formula (I) may be bacteriochlorins of Formula (Ib)

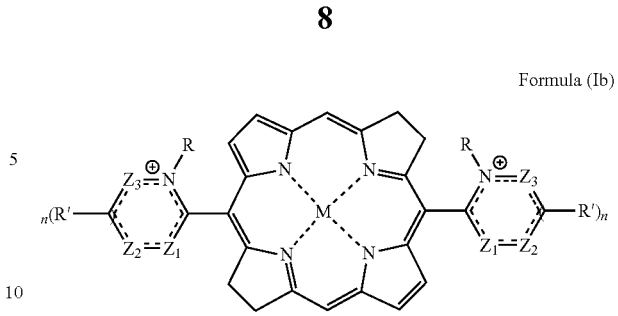

Formula (Ib)

wherein:

~~~~~~ represents a carbon-carbon single bond or a carbon-carbon double bond;

M is $H_2$ or a metal ion selected from Mg, Al, Si, Zn, Pd, Ag, In;

R is chosen from unsubstituted or substituted alkyl, unsubstituted or substituted heteroalkyl, unsubstituted or substituted aryl, unsubstituted or substituted heteroaryl, provided that R has fewer than 12 atoms;

For n=0, then $Z_1$, $Z_2$ and $Z_3$ are each independently chosen from oxygen or from YR", where Y are atoms in the ring each independently chosen from carbon, sulfur or nitrogen, and R" is bonded to Y and each independently chosen from hydrogen or from R;

For n=1, then $Z_1$, $Z_2$ and $Z_3$ are each independently chosen from YR", where Y are atoms in the ring each independently chosen from carbon, sulfur or nitrogen, R" is bonded to Y, and R' and R" are each independently chosen from hydrogen or from R; or pharmaceutically acceptable salts thereof.

Specific preferred compounds of the invention include the small cationic ortho-5,15-di-heteroaryl bacteriochlorin of Formula (Ib) where: M is $Zn^{2+}$, $Z_1$ is nitrogen, $Z_2$ and $Z_3$ are carbon, R is methyl, R' is hydrogen and R" is methyl or hydrogen, and n=0 which means that R' is not present in the structure.

Alternatively, the compounds of Formula (I) may be chlorins of formula (Ic)

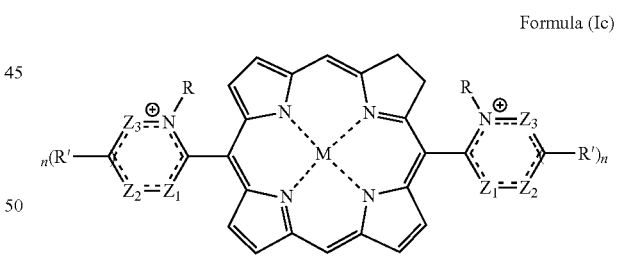

Formula (Ic)

wherein:

~~~~~~ represents a carbon-carbon single bond or a carbon-carbon double bond;

M is $H_2$ or a metal ion selected from Mg, Al, Si, Zn, Pd, Ag, In;

R is chosen from unsubstituted or substituted alkyl, unsubstituted or substituted heteroalkyl, unsubstituted or substituted aryl, unsubstituted or substituted heteroaryl, provided that R has fewer than 12 atoms;

For n=0, then $Z_1$, $Z_2$ and $Z_3$ are each independently chosen from oxygen or from YR", where Y are atoms in the ring each independently chosen from carbon, sulfur or nitrogen, and R" is bonded to Y and each independently chosen from hydrogen or from R;

For n=1, then $Z_1$, $Z_2$ and $Z_3$ are each independently chosen from YR", where Y are atoms in the ring each independently chosen from carbon, sulfur or nitrogen, R" is bonded to Y, and R' and R" are each independently chosen from hydrogen or from R; or pharmaceutically acceptable salts thereof.

Another aim of the present invention is to offer a method of preparation of compounds of Formula (I) in large quantities from affordable raw materials.

A further aim is to offer a medication to be used in photodynamic inactivation of microorganisms selected from the group consisting of: bacteria, fungi, yeasts, viruses or protozoa.

The present invention also relates to a pharmaceutically composition comprising at least one of the derivatives complying with Formula (I), or pharmaceutically acceptable salts thereof, a pharmaceutically acceptable carrier, and combination with a small molecular species and/or with an antimicrobial peptide which may potentiate the photoinactivation of microorganisms.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound of Formula (I) is administered in a pharmaceutically effective amount to a subject in need thereof in a pharmaceutical carrier by topical or intracavital application or by intralesional, intravenous, intramuscular, subcutaneous injection or by oral administration. A compound of the invention may be administered alone or in conjunction with a second, different therapeutic or adjuvant compound. By "in conjunction with" is meant together, substantially simultaneously or sequentially. The compound of the invention may be administered for a short course of treatment, such as for about one hour, one day or one week. In another embodiment, the compound of the invention may be administered over a longer period of time.

Various important factors contribute to determine the "pharmaceutically effective amount" of drug, light and oxygen required for photodynamic inactivation of microorganisms. Photodynamic inactivation relies on the combination of a photosensitizer, light of a wavelength absorbed by the photosensitizer and molecular oxygen. This combination leads to ROS and it is the "pharmaceutically effective amount" of ROS that determines the outcome of the therapy. Thus, this outcome depends on the dose of photosensitizer administered, on the dose of light delivered and on the oxygenation of the biological target. Of note, the drug-to-light interval, defined by the time between the administration of the photosensitizer and the illumination of the target, is also an important factor that contributes to determine the "pharmaceutically effective amount" because the arrival of the photosensitizer to the target, as well as its elimination or metabolism, will depend on time. For example, a very short drug-to-light interval—a few seconds—is likely to be insufficient to allow the photosensitizer to be on the target at the time of illumination and reduce the amount of ROS generated. The opposite example is a very long drug-to-light interval—a few weeks—which is likely to allow for the clearance of the photosensitizer from the biological target and reduce the amount of ROS generated. The fluence rate of the light (how many photons are delivered per unit area per unit time, is also an important factor to determine the outcome of the therapy because a very high fluence rate (too many photons too fast) may deplete the oxygen in the target ad render the therapy inefficient or ineffective.

In another embodiment, the invention provides a composition having a dosage range wherein the effective amount of the compound delineated herein (e.g., molecular species of Formula I) ranges from about 1 ng/kg to about 100 mg/kg. In certain embodiments, the effective amount of the compound of Formula (I) ranges from 100 ng/kg to 10 mg/kg. In a further embodiment, the effective amount of the compound delineate herein ranges from 500 ng/kg to 5 mg/kg and the light dose ranges from 0.1 to 300 J/cm². In a further embodiment, the effective amount of the compound delineated herein ranges from about 500 ng/kg to 5 mg/kg, the light dose is between 1 and 100 J/cm² and the drug-to-light interval is selected from concomitant with the administration of the photosensitizer to one week after the administration of the photosensitizer.

Another object of the present invention is a kit comprising a pharmaceutical composition delineated herein and instructions for administration of the composition. The kit may provide the pharmaceutical composition in any suitable container (i.e., vial, bottle, syringe, ampoule, tube), optionally contain a light source, and include instructions such as for photodynamic therapy/inactivation (e.g., light exposure instructions, drug-to-light recommendations)

Other aims and technical features will appear in the following description that is given only by way of example and without being limited thereto.

In view of the shortcomings of the current photosensitizers employed in PDI to penetrate biofilms and photoinactivate microorganisms at concentrations lower than 1 mg/kg without toxicity to the host, the present invention discloses new porphyrin derivatives that combine small size with strong absorption of light, high photostability, high quantum yields of ROS photogeneration, appropriate distribution of positive charges and biocompatibility. One of the technical characteristics of these derivatives lies in their small size and the consequent ability to diffuse through the porin channels and rapidly diffuse in biofilms. Another technical advantage is the preservation of the porphyrin, chlorin or bacteriochlorin macrocycle known for its strong absorption of light and ability to generate ROS in high quantum yields. Yet another advantage is the presence of substituent groups that enhance the photostability of the porphyrin derivatives and impart enough positive charge to make them selective towards microorganisms. A further technical characteristic of porphyrin derivatives with Formula (I) is that they are significantly fluorescence, namely with fluorescence quantum yields higher than 0.1, which allows for their non-invasive visualization in the target. This visualization is a desired property because it enables the visualization of the target and the choice of the best timing to start the therapy, for instance when the photosensitizer accumulated in the target. A most preferred property of the new porphyrin derivatives disclosed in the present invention is the distribution of the positive charge around the macrocycle, which favor the exposure of the excess of positive charge to the environment and the interaction of the photosensitizer with the outer membranes of microorganisms. This unsuspected property is determinant to increase the phototoxicity towards microorganisms and reduce the toxicity towards human cells, leading to highly phototoxic small photosensitizers targeted to the inactivation of microorganisms.

BRIEF DESCRIPTION OF THE DRAWINGS

Without intent to limit the disclosure herein, this application presents attached drawings of illustrated embodiments for an easier understanding.

DESCRIPTION OF THE EMBODIMENTS

Figure 1:
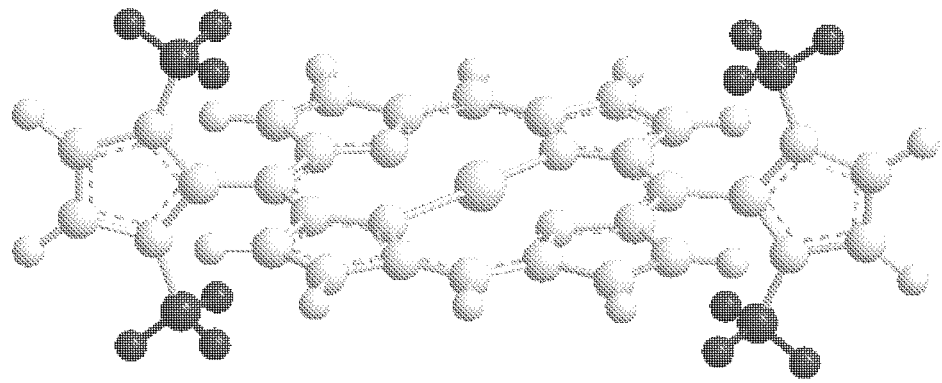
FIG. 1: Chem 3D minimized structure of Formula (IIa) where the atoms shown in black have an excess of positive charge
Figure 2:
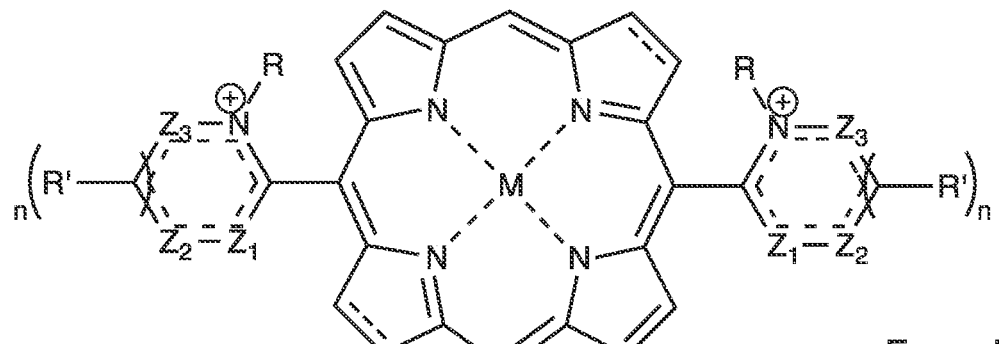
FIG. 2: Structures of the molecular species of Formula (I), (Ia), (Ib) and (Ic).
Figure 2:
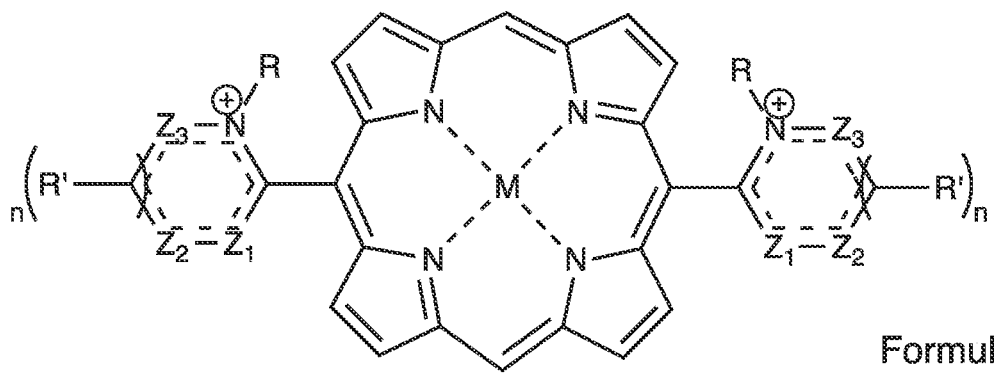
Figure 2:
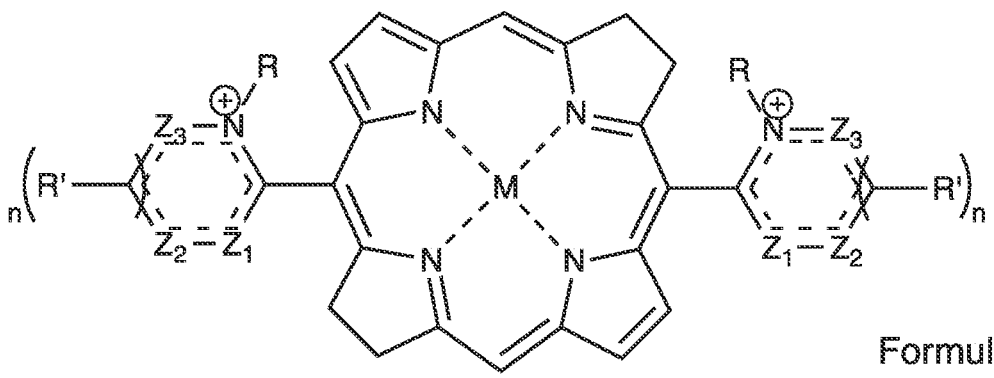
Figure 2:
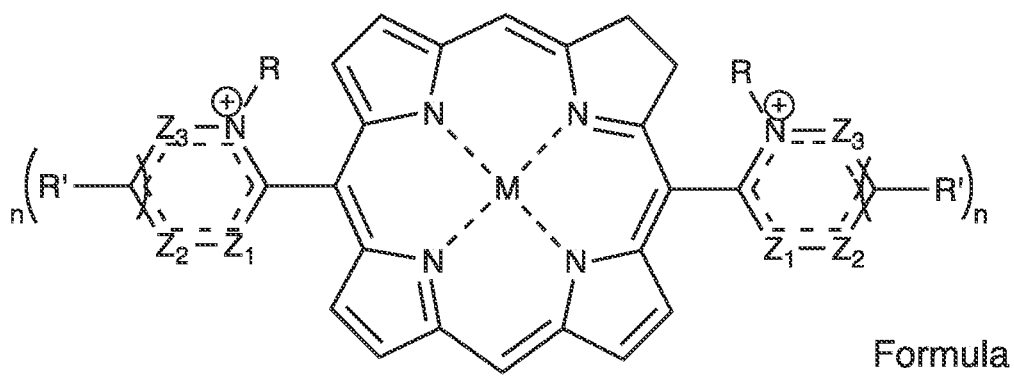
Figure 3:
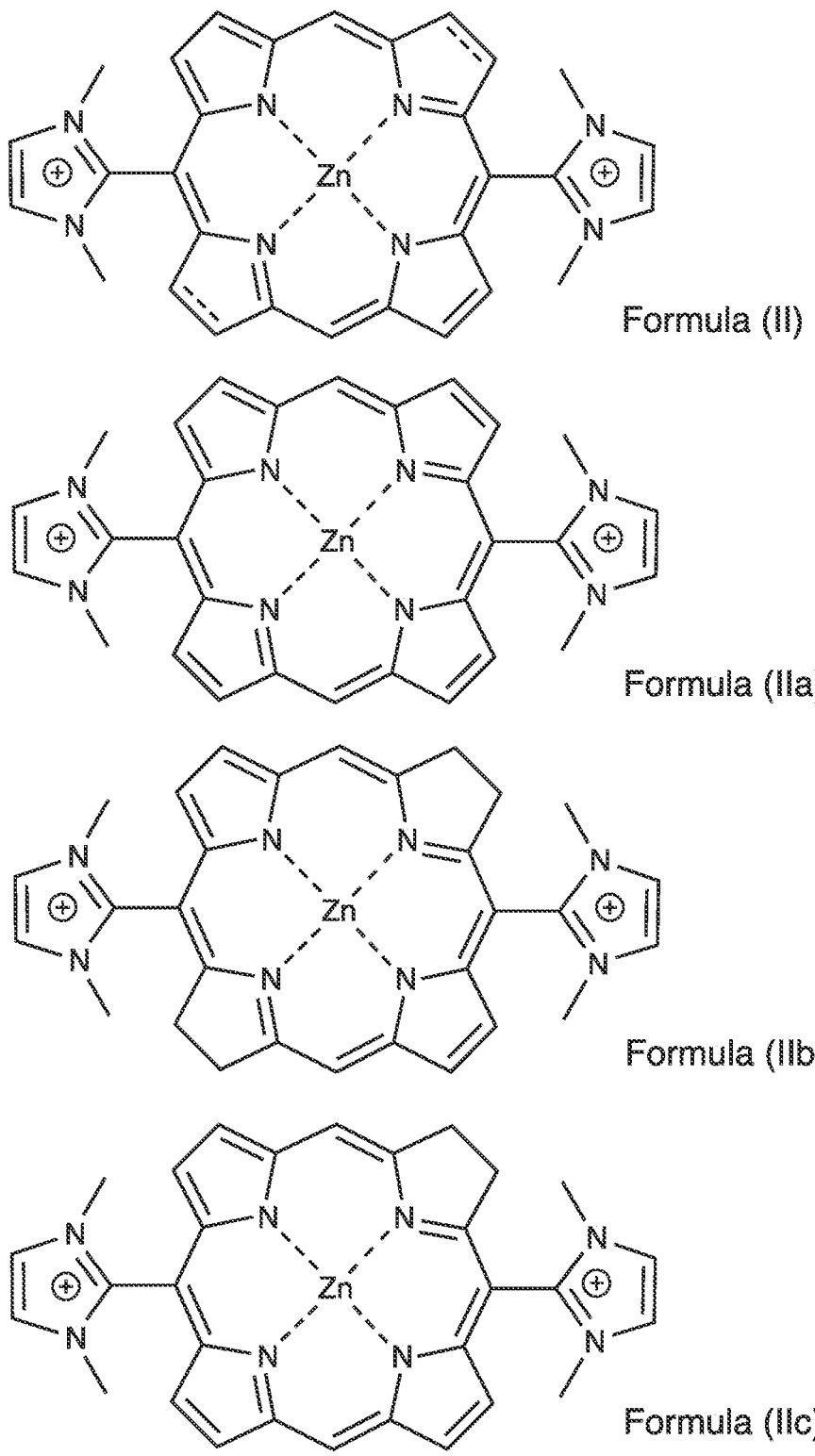
FIG. 3: Structures of the molecular species of Formula (II), (IIa), (IIb) and (IIc).
Figure 4:
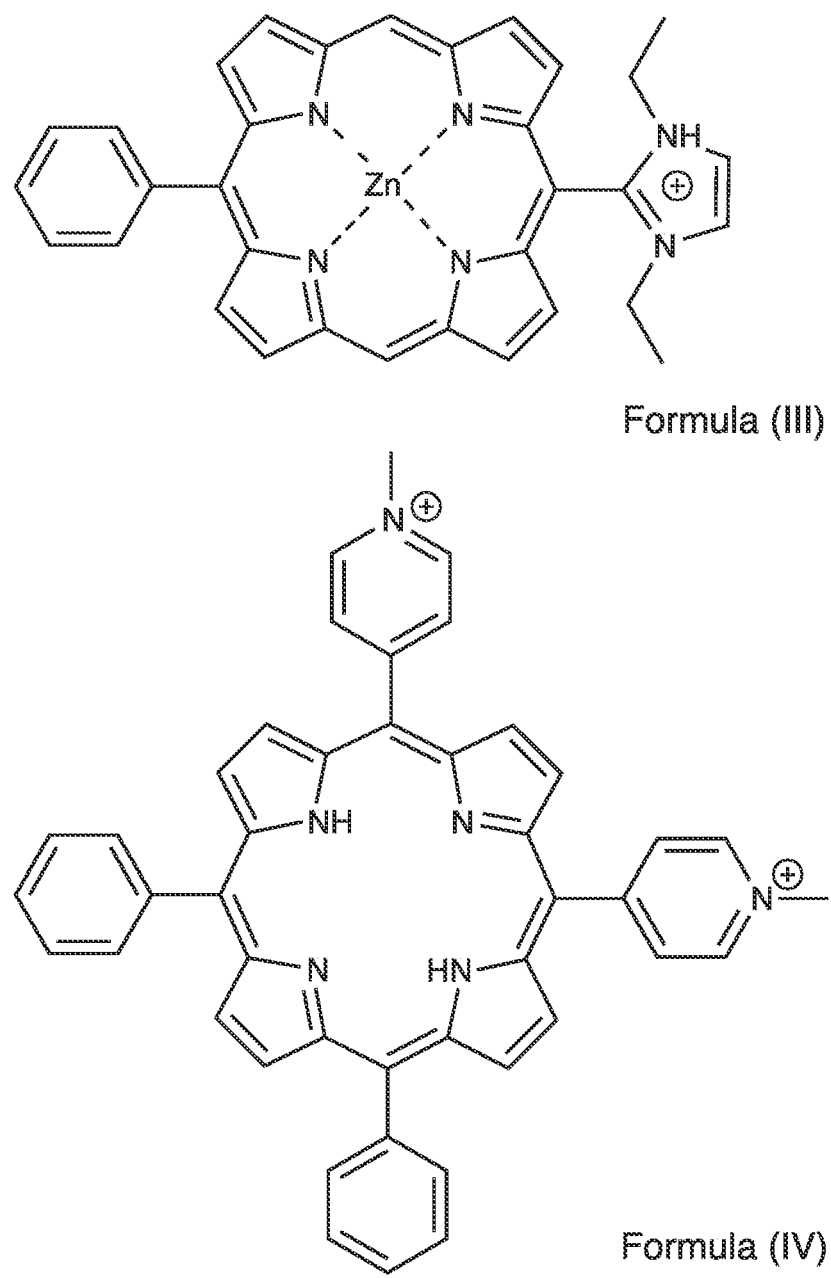
FIG. 4: Structures of the molecular species of Formula (III) and (IV).

Referring to the drawings, herein are described optional embodiments in more detail, which however are not intended to limit the scope of the present application.

A. Materials and Methods

All solvents were dried according to standard procedures. All commercial reagents were purchased from Sigma-Aldrich and Fluorochem and used without further purification. The $^1$H and $^{13}$C nuclear magnetic resonance (NMR) spectra were recorded on a 400 Bruker Avance spectrometer (400 and 101 MHz, respectively), using tetramethylsilane ($\delta$=0.00 ppm) as internal standard for $^1$H and $^{13}$C. The electrospray ionization (ESI) mass spectra were obtained at the Mass Spectrometry Unit (UniMS), ITQB/iBET, Oeiras, Portugal.

Optical Absorption: The ultra-violet visible optical absorption (UV-vis) spectra used in the control of the synthesis were recorded on Hitachi U-2001 or Shimadzu 2100 spectrophotometers using spectroscopic grade solvents. The UV-Vis-NIR optical absorption was recorded with an Agilent Cary5000 UV-Vis-NIR Spectrophotometer in the determination of the molar absorption coefficient and with Shimadzu UV-2100 spectrometer in routine measurements. The absorption spectra were recorded in the wavelengths from 300 nm up to 800 nm. Molar absorption coefficients were determined by using Beer-Lambert's law. For each compound, a minimum of 6 solutions were prepared in concentrations ranging from 10$^{-7}$ to 10$^{-6}$ M, giving absorbance values between 0.1 and 1.

Fluorescence Emission: The fluorescence emission spectra were recorded in a Horiba Scientific Spectrofluorometer Fluoromax-4. The spectra were collected from 550 nm up to 800 nm using standard cuvettes of 1 cm of optical path. Fluorescence quantum yields ($\Phi_F$) were obtained comparing the area of integrated fluorescence of the samples with that of a reference fluorimetric compound with known $\Phi_F$, corrected by the absorption of sample and reference at the excitation wavelength and by the refractive indices of the solvents used for the standard and reference solution. Tetraphenylporphyrin (TPP) in toluene ($\Phi_F$=0.11) was used as standard. The absorbance of the solutions at the excitation wavelength was 0.01.

Singlet Oxygen Quantum Yield: The experiments were run at room temperature. The solutions were excited at 355 nm using a Nd-YAG laser (Spectra-Physics Quanta-Ray GRC-130) and the phosphorescence of singlet oxygen collected at 1270 nm in a Hamamatsu R5509-42 photomultiplier, cooled to 193 K in a liquid nitrogen chamber, after selection of the wavelength with a monochromator with 600 lines grading. A Newport filter model 10LWF-1000-B was used in the emission to avoid scattering and fluorescence. Phenalenone was used as a reference of singlet oxygen generator, $\Phi_\Delta^{Ref}$=0.98. Extrapolating to time-zero the decays of the singlet molecular oxygen emissions measured for sample and the reference solutions at a given laser intensity, we obtained a relation between emission intensities as a function of laser intensity, that is identical to the relation between the singlet molecular oxygen quantum yields. The singlet oxygen quantum yields were obtained by comparing the linear dependence between and the energy of the laser pulse for both the sample and the reference for the same absorption of sample and reference at the excitation wavelength, taking into account the singlet oxygen quantum yield of phenalenone.

n-Octanol:PBS partition ratio: a modification of the shake-flask method was employed to determine the equilibrium concentrations of the photosensitizer in n-octanol and in phosphate-buffered saline (PBS) mixed in equal volumes, using the typical fluorescence band of the same photosensitizer and the ratio of the fluorescences after dilution by the same factor with dimethylsulfoxide.

Photobleaching experiments: Photodecomposition experiments were made dissolving the photosensitizers in water with 9% dimethylsulfoxide. A volume of 3 mL was placed in a cuvette and irradiated ensuring that all the light hits the solution. The porphyrins were irradiated using a LED light with emission at 415 nm and an effective output power of 0.27 mW. Photodecomposition quantum yield ($\Phi_{pd}$) is defined as the ratio between the rate of disappearance of photosensitizer molecules $v_d$ and the rate of absorption of photons $v_p$.

Phototoxicity towards bacteria was evaluated in vitro. Assays were performed with the following bacteria: *Escherichia coli* ATCC 25922, *Pseudomonas aeruginosa* ATCC 27853 and *Staphylococcus aureus* ATCC 29213. Further assay were performed with clinical antibiotic-resistant strains from the Centro Hospitalar da Universidade de Coimbra, namely *Staphylococcus aureus* methicillin-resistant (MRSA) strain Sa1CHUC recovered from the skin of a burnt patient (resistant to all beta-lactamic antibiotics), and *Acinetobacter baumannii* 141HUC isolated from an exudate of a burn wound and highly resistant to all beta-lactamics (penicillins, cephalosporins, monobactams and carbapenems), quinolones and the aminoglycosides gentamicin and netilmicin. The planktonic bacteria cells were cultured in Mueller Hinton (MH) agar (Sigma Aldrich) at 37° C. overnight. Cell density was adjusted to the 0.5 McFarland standard in sterile water, which corresponds to approximately $1.5 \times 10^8$ CFU/mL. For PDI experiments cell suspensions of bacteria were incubated with various concentrations of the photosensitizers for 1 h, in the dark, at room temperature, using a 96 well plate. Then, the plate was illuminated with a blue light LED (420 nm, 4 mJ/s). Cells incubated with photosensitizers in the dark were covered with aluminum foil for the same time as the PDI groups (1 h). After illumination (or dark incubation) samples were shaken, diluted in PBS and mixed. Aliquots were taken from each well and streaked in MH agar in duplicate for CFU determination and incubated for 37° C./18-24 h in the dark. After 24 h, the colonies were counted and CFU determined. The experiments were performed in triplicate. Statistical analysis was performed with GraphPad Prism 6.

Phototoxicity towards biofilms was evaluated after biofilm growth overnight. Assays were performed with biofilms from *Staphylococcus aureus* ATCC 25925. Initially, bacteria cultures were diluted 1:9 in Brain Heart Infusion (BHI) (Kasvi®, Brazil). The microorganisms were centrifuged (1500 rpm, 10 min) and washed twice with phosphate-buffered saline (PBS). Aliquots of the diluted bacterial suspensions were inoculated into 24-well flat-bottom sterile polystyrene microplates and incubated for 24 h at 37° C. For PDI experiments, the plates with biofilms were incubated with 5.2 nM of the photosensitizer for 30 min in the dark at room temperature. Wells used as controls were incubated with PBS only. After that, the plates were illuminated with a specially designed light source named Biotable®. The Biotable® was composed by 24 LED lamps that deliver a uniform light fluence rate of 30 mW/cm² in the wavelength range between 400-650 rm. Wells used as controls were incubated with PBS only. Cells incubated with photosensitizers in the dark were covered with aluminum foil for the same time as the PDI cells (1 h). Following irradiation (or dark control), photosensitizer was carefully removed from the wells and the biofilms were washed once with PBS. The biofilms were scraped carefully, sonicated and then vortexed to homogenize the samples. Treated and untreated samples were serially diluted, plated on the MH petri dishes, and incubated for 24 h at 37° C. in the dark to allow colony formation. After this time, the colonies were counted and the colony-forming units (CFU) determined.

Toxicity towards human cell lines was evaluated in vitro using the 3-(4,5-dimethylthiazol-2-yl)2,5-diphenyl tetrazolium bromide (MTT, from Sigma Aldrich) assay to estimate the viability of cells after appropriate treatment. After cell attachment, photosensitizer solutions in PBS at concentrations between 0 to 10 µM were added to the cell cultures and incubated for 1 h at 37° C. in the dark. After illumination with the Biotable® or after the equivalent time in control experiments, MTT dissolved at 5 mg/ml in PBS was added to each well (final concentration 0.5 mg/ml), and the microplates were further incubated for 3-4 hours. Medium were then discarded and 100 µl of methanol were added to the cultures and mixed thoroughly to dissolve the dark blue crystals of formazan. Formazan quantification was performed using an automatic microplate reader (Multiskan Go Thermo) by absorbance measurements at 570 nm. Each experiment was repeated three times. Data were expressed as mean absorbance value of six samples and standard error of the mean.

Confocal microscopy images were acquired using a Zeiss fluorescence confocal microscope (LSM 780 inverted model) with laser excitation (LASER Diode 405 nm). The microscope is equipped with high sensitivity GaAsP detectors for spectral imaging (400-700 nm).

B. Description of Methods of Preparation of the Compounds Precursors

Figure 5:
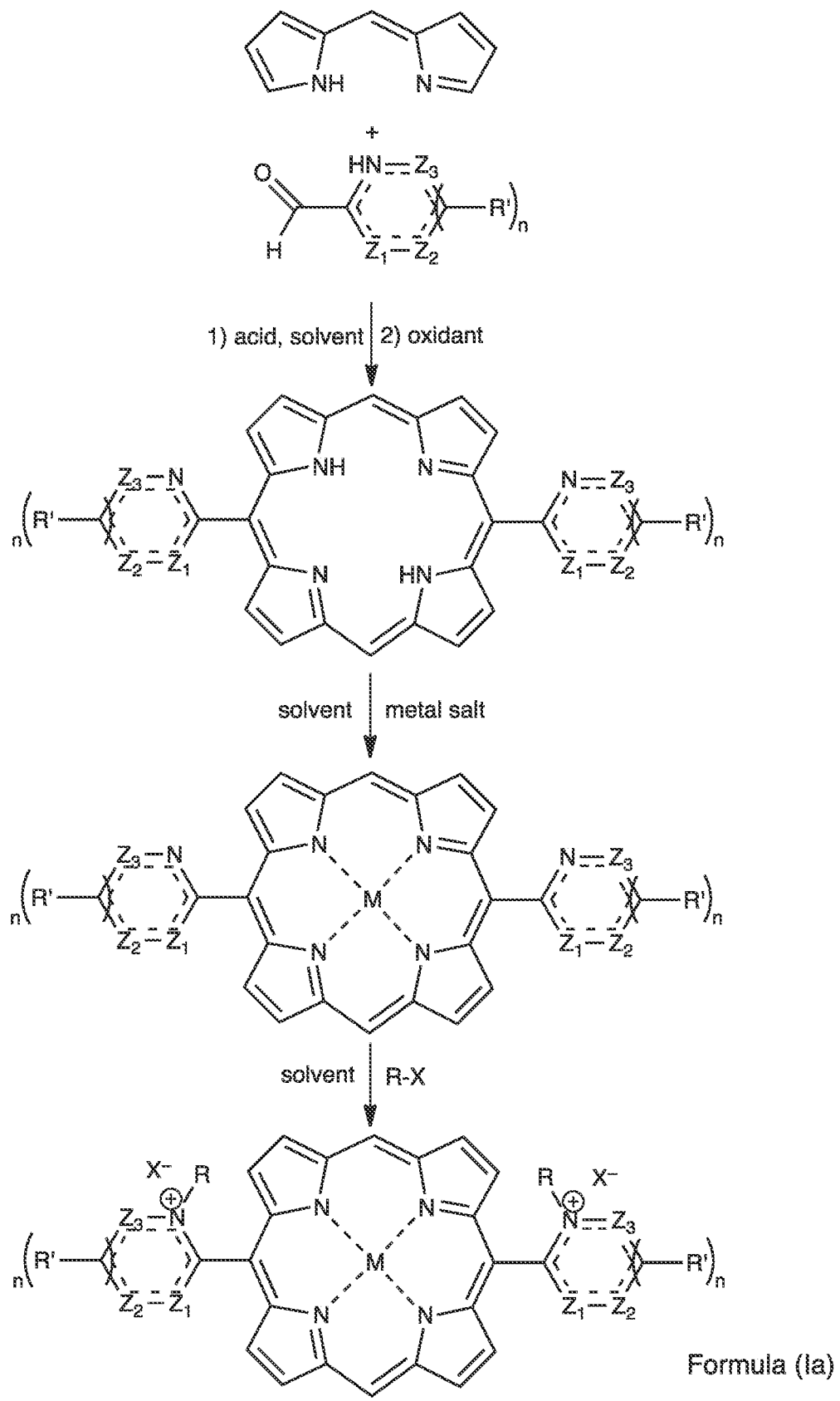
FIG. 5. General synthetic approach for the synthesis of precursors and compounds of Formula (Ia)
Figure 6:
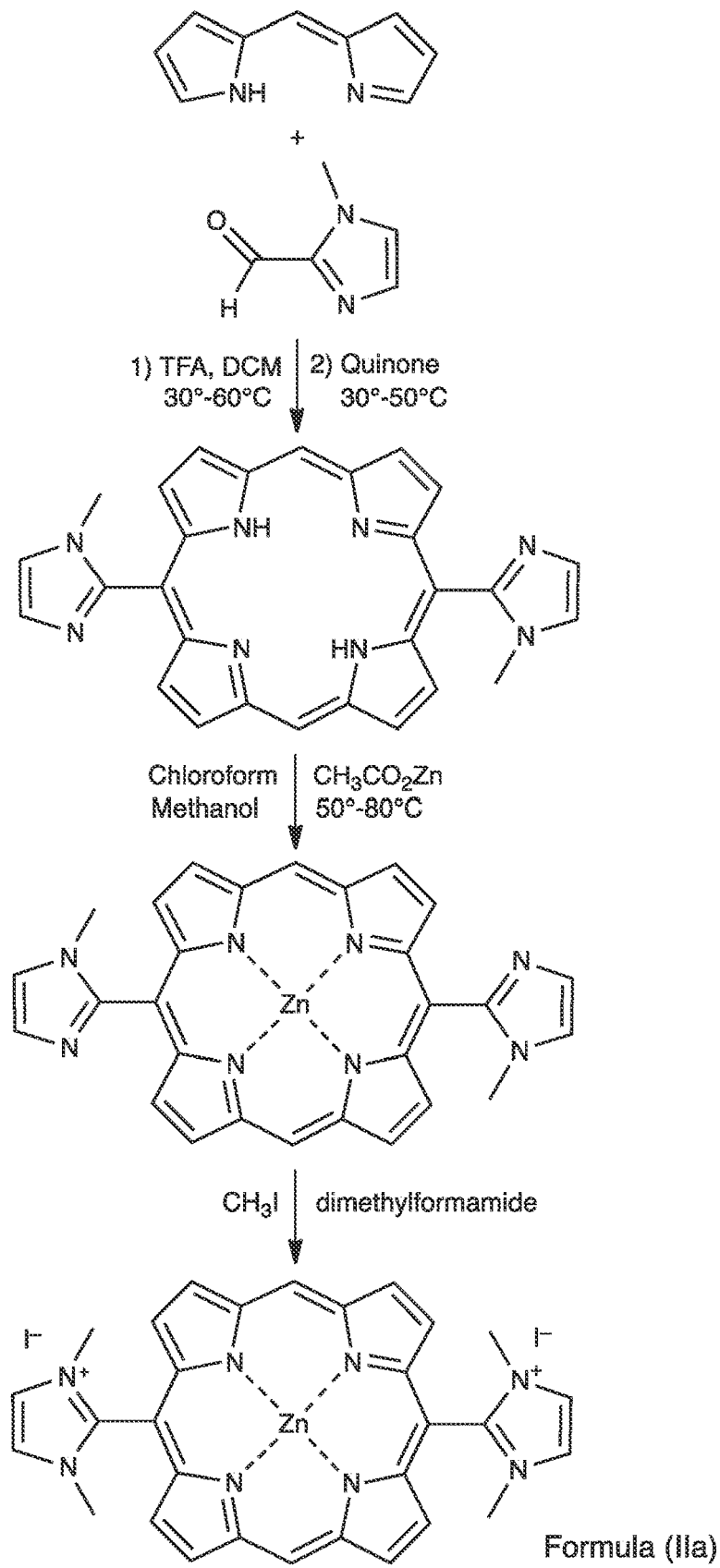
FIG. 6. General synthetic approach for the synthesis of precursors and compounds of Formula (IIa)

The general scheme for the preparation of porphyrin precursors is depicted below (FIG. 5):

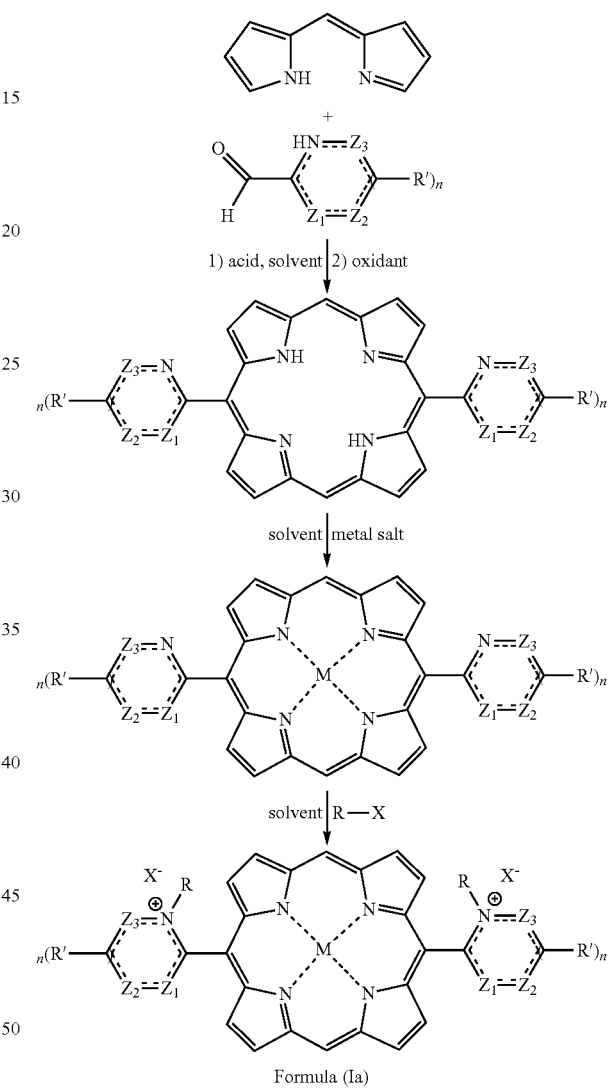

Formula (Ia)

Non-symmetric 5,15-disubstituted porphyrins precursors were prepared by mixture of equimolar amounts of commercially available dipyrromethane (Harvechem) with the desired heteroaromatic aldehyde dissolved in an appropriate solvent. The solvent was degassed with an inert gas and selected from dichloromethane, chloroform, carbon tetrachloride, toluene, dioxane, N-methyl-2-pyrrolidone, tetrahydrofuran or dimethoxyethane. Then, an acid was added as catalyst which was selected from organic, namely trifluoroacetic acid, p-toluenosulfonic acid, tricloroacetic acid, or inorganic namely, aluminosilicate (Al—NaY) or sulfonic clay. The reaction vessel was shielded from ambient light and stirred under inert gas, for 15 min to 6 hours, at temperature between 0° C. and 50° C. The cyclization to porphyrinogen was monitored by thin-layer chromatography (TLC). Then, the porphyrinogen was oxidized to the correspondent porphyrin. The appropriate amount of oxidant was chosen from $O_2$, $O_2$/light, nitrobenzene/organic acid (acids from 2 to 13 carbon atoms) or preferentially from high potential quinones, namely 2,3-dichloro-5,6-dicyano-1,4-benzoquinone (DDQ) or 2,3,5,6-tetracyano-1,4-benzoquinone, for 5 min to 10 hours, at temperature between 25° C. to 100° C. After solvent removing, the crude was dissolved in the appropriate solvent (dichloromethane, chloroform, carbon tetrachloride, toluene, dioxane, N-methyl-2-pyrrolidone, tetrahydrofuran, dimethoxyethane) and washed with a saturated solution of an appropriate base. The base can be inorganic and selected from carbonates, phosphates or organic, or can be selected from amines, preferentially trimethylamine. After that, a silica gel column chromatography was performed, using the appropriate solvent mixture (solvents can be selected from: dichloromethane, chloroform, carbon tetrachloride, toluene, dioxane, tetrahydrofuran, dimethoxyethane, ethyl ether, ethyl acetate, methanol, ethanol).

Non-symmetric metal complexes precursors of 5,15-dissubstituted porphyrin were prepared by reaction of 5,15-dissubstituted porphyrin with the selected metal salt. The 5,15-dissubstituted porphyrin was dissolved in the appropriate solvent, selected from dichloromethane, chloroform, carbon tetrachloride, toluene, dioxane, N-methyl-2-pyrrolidone, tetrahydrofuran, dimethoxyethane; dimethylformamide, and an excess (1-50 equivalents) of the selected metal salt is added. The metal salt was selected from magnesium dichloride, magnesium acetate, aluminium trichloride; zinc acetate, zinc chloride; palladium acetate, palladium dichloride, silver acetate, silver chloride; indium trichloride, indium acetate or trichlorosilane. Then, the reaction was heated up at temperatures between −25° C. to 200° C. The complexation was monitored by UV-vis and thin-layer chromatography (TLC). Once complete, the solvent was removed and the solid dissolved in the appropriate solvent, selected from dichloromethane, chloroform, carbon tetrachloride, toluene, tetrahydrofuran, ethyl ether or ethyl acetate, and the impurities are extracted with water (3-7 times). The organic layer was dried using an inorganic drying agent selected from anhydrous sodium sulfate, sodium sulfate, anhydrous calcium sulfate; anhydrous calcium sulfate; anhydrous calcium oxide. After decantation, the organic solvent was evaporated, and pure metal complex was isolated.

Synthesis of Cationic ortho-5,15-di-heteroaryl porphyrins

The cationic ortho-5,15-di-heteroaryl porphyrin (Formula Ia; M=2H) was achieved via alkylation of ortho-nitrogen atom (Formula Ia, R) using the selected halogenated substituted or unsubstituted alkyl, heteroalkyl, aryl, heteroaryl (R≤12 atoms). The selected precursor 5,15-di-heteroaryl porphyrin was dissolved in a solvent, selected from dichloromethane, chloroform, carbon tetrachloride, toluene, dioxane, N-methyl-2-pyrrolidone, tetrahydrofuran, dimethoxyethane; dimethylformamide and an excess (2 to 100 equivalents) of the selected halogenated substituted or unsubstituted alkyl, heteroalkyl, aryl, heteroaryl was added. The reaction was maintained at temperature between 20° C. and 100° C. for 1 to 96 hours. The progress of the reaction was followed by TLC. 5,15-di-heteroaryl porphyrin (Formula Ia; M=2H) was precipitated with a selected solvent.

The solvent was selected from an apolar solvent namely, diethyl ether, dichloromethane, hexane, pentane, chloroform. The solid was filtrated and recrystallized from the selected solvent (methanol, ethanol, propanone, ethyl acetate) and pure cationic ortho-5,15-di-heteroaryl porphyrins (Formula I; M=2H) were isolated.

Synthesis of Metal Complexes of Cationic ortho-5,15-di-heteroaryl porphyrins

The metal complexes of cationic ortho-5,15-di-heteroaryl porphyrin derivatives (Formula I; M=Mg, Al, Zn, Pd, Ag, In) were synthetized via alkylation of ortho-nitrogen atom (Formula Ia, R) using the selected halogenated alkyl, heteroalkyl, aryl, heteroaryl (R≤12 atoms). The selected metal complex of 5,15-di-heteroaryl porphyrin precursor was dissolved in a solvent, selected from dichloromethane, chloroform, carbon tetrachloride, toluene, dioxane, N-methyl-2-pyrrolidone, tetrahydrofuran, dimethoxyethane; dimethylformamide and an excess (2 to 100 equivalents) of the selected halogenated alkyl, heteroalkyl, aryl, heteroaryl was added. The reaction was maintained at temperature between 20° C. and 100° C. for 1 to 96 hours. The evolution of the reaction was followed by TLC. The product 5,15-bis (1,3-dimethylimidazol-2-yl)porphyrinate (Formula I; M=Mg, Al, Zn, Pd, Ag, In) was precipitated with a selected solvent. The solvent was selected from an apolar solvent namely, diethyl ether, dichloromethane, hexane, pentane, chloroform. The solid was filtrated and recrystallized from the selected solvent (methanol, ethanol, propanone, ethyl acetate) and pure cationic ortho-5,10-di-heteroaryl porphyrins (Formula I; M=Mg, Al, Zn, Pd, Ag, In) were isolated.

Synthesis of Cationic ortho-5,15-di-heteroaryl bacteriochlorins (Formula Ib)

The cationic ortho-5,15-di-heteroaryl porphyrin derivatives were used as precursors to obtain the corresponding reduced bacteriochlorins. The reduction was based on the diimide reduction method using hydrazide as the hydrogen source, preferably using p-toluenesulfonyl hydrazide (p-TSH), inorganic or hindered organic bases, in solvents selected from dioxane, N-methyl-2-pyrrolidone, tetrahydrofuran, dimethoxyethane, dimethylformamide, pyridine and picoline, using a modification of the method disclosed in PCT/EP2005/012212 (16). The reduction can also take place in the absence of solvents and in the absence of bases, using a modification of the method disclosed in PCT/PT2009/000057 (17). After cooling (room temperature) the solid was dissolved in water and the excess of hydrazide was removed using Amicon device with membranes with the appropriated molecular weight cut-offs. The water was lyophilized, the solid obtained recrystallized from the selected solvent (methanol, ethanol, propanone, ethyl acetate) and pure cationic ortho-5,15-di-heteroaryl bacteriochlorins were isolated.

Synthesis of Cationic ortho-5,15-di-heteroaryl chlorins (Formula Ic)

The cationic ortho-5,15-di-heteroaryl porphyrins were used to obtain the corresponding reduced chlorins. The reduction was based on the diimide reduction method using hydrazide as the hydrogen source, preferably using p-toluenesulfonyl hydrazide (p-TSH), inorganic or hindered organic bases, in solvents selected from dioxane, N-methyl-2-pyrrolidone, tetrahydrofuran, dimethoxyethane, dimethylformamide, pyridine and picoline, using a modification of the method disclosed in PCT/EP2005/012212 (16). The reduction can also take place in the absence of solvents and in the absence of bases, using a modification of the method disclosed in PCT/PT2009/000057 (17). After cooling (room temperature) the solid was dissolved in water and the excess of hydrazide was removed using Amicon device with membranes with the appropriated molecular weight cut-offs. A mixture of chlorin and small amounts of bacteriochlorin was obtained. The mixture of chlorin and small amounts of bacteriochlorin was dissolved in an appropriated solvent selected from dioxane, N-methyl-2-pyrrolidone, tetrahydrofuran, dimethoxyethane, dimethylformamide and oxidized to the corresponding chlorin. The oxidation was performed by heating the mixture at 20° C. to 100° C. in the presence of air or by adding $FeCl_3 \cdot 6H_2O$ (0.5-10 equivalents) followed by hydrogen peroxide (3% in water, 0.1-10 mL). The final solution was kept under stirring, at room temperature for 30 minutes to 6 hours. Once complete, the solvent was removed and the solid dissolved in in water and the excess of hydrazide was removed using Amicon device with membranes with the appropriated molecular weight cut-offs. The water was lyophilized, the solid obtained recrystallized from the selected solvent (methanol, ethanol, propanone, ethyl acetate) and cationic ortho-5,15-di-heteroaryl chlorins (Formula Ic) were isolated.

C. Properties of the Compounds

The absorptivities of the compounds and other photophysical and photobiological properties were measured as described in the Materials and Methods. The wavelength of maximum absorption in the infrared did not vary in the concentration range studied. This is indicative of negligible aggregation between the molecules, which exist mostly as monomers at the studied concentrations in the selected solvents. Table 1 presents the molar absorption coefficient ($\varepsilon_{max}$) of the most intense absorption band of a typical cationic ortho-5,15-di-heteroaryl porphyrin derivative of Formula (I), more specifically, of the porphyrin derivative of Formula (IIa) in water with 9% dimethylsulfoxide. The same table also presents the fluorescence quantum yield ($\Phi_F$), singlet oxygen generation ($\Phi_\Delta$) and the logarithm of the n-octanol:water partition coefficient (log $P_{OW}$). The phototoxicity of the same derivative are also presented in Table 1 for human fibroblast and human keratinocyte cell lines. Table 2 presents the phototoxicity towards bacteria, including multidrug-resistant strains and bacteria in biofilms, described in the Materials and Methods.

TABLE 1

Photophysical and photochemical properties of the cationic ortho-5,15-di-heteroaryl porphyrin derivative of Formula (IIa), together with phototoxicity towards human fibroblast and human keratinocyte cell lines for a light dose of 5 J/cm².

| λ | | | | | Survival fraction at 10 μM | |
|---|---|---|---|---|---|---|
| nm | $\varepsilon(\lambda)/10^3$ $M^{-1} cm^{-1}$ | $\Phi_F$ | $\Phi_\Delta$ | log $P_{ow}$ | Fibroblast | Keratinocytes |
| 407 | >20 | 0.10 | 0.75 | −1.16 | 100% | 80% |

TABLE 2

Photobiological properties the cationic ortho-5,15-di-heteroaryl porphyrin derivative of Formula (IIa) in planktonic bacteria under 1.36 J/cm² at 415 nm and in bacterial biofilms under 5 J/cm² in the wavelength range between 400-650 nm.

| log CFU at 1 μM | | | | | log CFU at 5.2 nM |
|---|---|---|---|---|---|
| S. Aureus | E. Coli | P. Aerogirosa | S. Aureus MRSA | Acinetobacter 141Hu | S. Aureus biofilm |
| 7 | 7 | 3 | 7 | 7 | 7 |

The intensity of its longest wavelength absorption band at 622 nm decreased by less than ΔA=0.001 after 15,000 second of illumination corresponding to an effective absorption of ca. 4 J. This places an upper limit of 0.001 to the photodecomposition quantum yield.

The typical photophysical, photochemical and photobiological properties of cationic ortho-5,15-di-heteroaryl porphyrin derivative of Formula (I) remedy the shortcoming aforementioned of current photosensitizers employed in PDI of microorganisms. In particular, the molecular species of Formula (I) can have small size, proper distribution of positive charge, solubility in biocompatible vehicles, intense light absorption, moderate fluorescence for convenient monitoring and very sigh singlet oxygen quantum yields.

The conjugation of photostability, strong absorption in the phototherapeutic window, high yield of ROS and proper distribution of positive charge density offers another advantageous technical characteristic to the porphyrin derivatives of formula (I): very low phototoxicity towards human cells but very high phototoxicity towards bacteria. Table 1 shows an example of a photosensitizer according to Formula (I) that incubated in a 10 μM concentration with human fibroblast and human keratinocyte cell lines under a light dose of 5 J/cm² has very low phototoxicity: more 80% of the human cells survive these conditions. However, when incubated at 1 μM concentration with Gram-negative S. Aureus or Gram-negative E. Coli and exposed to 1.36 J/cm² or light at 415 nm, the number of bacterial CFU is reduced by 7 orders of magnitude. More importantly, the same happens when said photosensitizer is used in PDI of a methicillin-resistant Staphylococcus aureus strain or an Acinetobacter baumannii strain highly resistant all beta-lactamics, including carbapenems, quinolones, gentamicin and netilmicin. The phototoxicity against a Staphylococcus aureus biofilm is even more impressive: incubation with a ca. 5 nM concentration of said photosensitizer followed by exposure to 5 J/cm² of white light to leads to a 7 orders of magnitude reduction of bacteria in the biofilm.

The ability of porphyrin derivatives of Formula (I) to diffuse rapidly to they target, combined with their low phototoxicity towards human cells and high phototoxicity towards microorganisms, make these porphyrin derivatives especially suitable for antimicrobial and/or antiviral and/or anti-fungi and/or anti-yeasts and/or anti-protozoa medications for human or animal usage exhibiting as a main active agent one or several porphyrin derivatives described in the present invention. This type of medication, used in particular in PDI, may also contain one or several pharmaceutically acceptable excipients. Additionally, the formulation may contain small molecule inhibitors of pathogen efflux systems and/or a small polycationic molecular species that disrupts the outer membrane of the microorganism and/or an antimicrobial peptide and/or a species that undergoes electron transfer to the photosensitizer triplet state to generate reactive radicals and potentiate the photodynamic inactivation o the microorganism.

The reactive oxygen species generated by the illuminated photosensitizer molecules trigger a cascade of chemical and biological processes that culminate in the death of the bacteria and/or viruses and/or fungi and/or yeasts and/or protozoa.

The compounds of the present invention may also fluoresce with reasonable quantum yields and in the phototherapeutic window. Table 1 presents an example of a photosensitizer with $\Phi_F$=0.10. This typical fluorescence can be used to detect the presence of the compound in the target tissue and offers the possibility of using the compounds of the present invention for the visualization of infections originated by microorganisms.

EXAMPLES

This invention will now be described in more detail in the following non-limiting EXAMPLES.

Example 1. Procedure for the Preparation of 5,15-bis(1,3-dimethylimidazol-2-yl)porphyrinate zinc (II) diiodide

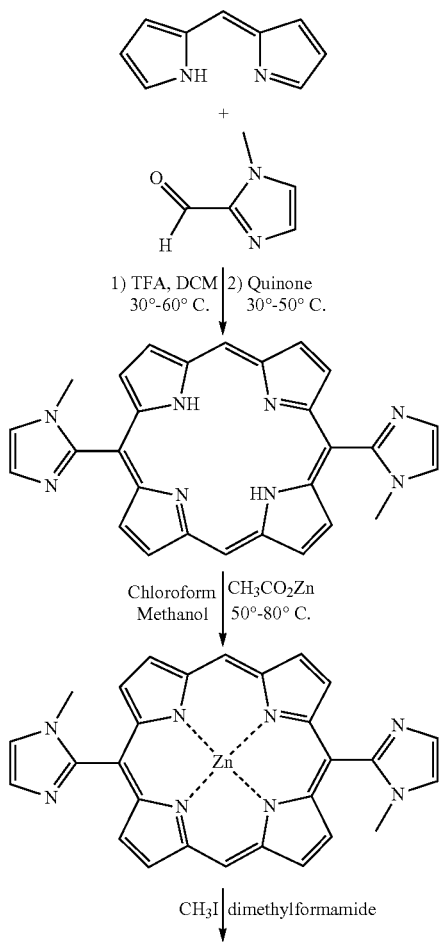

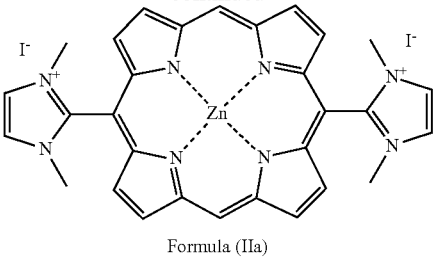

Formula (IIa)

A solution of commercial dipyrromethane (438 mg, 3 mmol) and 1-methylimidazole-2-carboxaldehyde (330 mg, 3 mmol) in $CH_2Cl_2$ (300 ml) was degassed with a continuous stream of argon, for 10 min, before addition of catalytic amounts of TFA (153 μL, 2 mmol). The reaction vessel was shielded from ambient light and stirred under argon, for 3 hours, at T=25° C. Then, 2,3-dichloro-5,6-dicyano-1,4-benzoquinone (DDQ) (2.04 g, 6 mmol) was added, at once, to the reaction mixture, and stirring at temperature of 30-50° C. was pursued for 1 hour. After removal of the solvent, the crude was dissolved in $CH_2Cl_2$ and washed with a saturated solution of sodium bicarbonate. After that, a silica gel column chromatography was performed, using dichloromethane/methanol (10:1) as eluent. After solvent evaporation 5,15-bis(1-methylimidazol-2-yl)porphyrin was isolated and after drying, under vacuum, with 19% yield (0.134 g). $^1$H NMR (400 MHz, $CDCl_3$): δ mixture of atropoisomers 10.35 (s, 2H), 9.43 (d, J=4.3 Hz, 4H), 9.03 (d, J=4.3 Hz, 4H), 7.73 (d, J=10.7 Hz, 2H), 7.54 (s, 2H), 3.52 (s, 6H), −3.31 (s, 2H). UV-vis ($CH_2Cl_2$): $\lambda_{max}$/nm (log ε): 406 (4.83), 500 (3.75), 535 (3.54), 573 (3.37), 627 (3.12). ESI-MS [M+H]+ ($CH_2Cl_2$), m/z: 471.20405; calculated for $[C_{28}H_{23}N_8]^+$: 471.20402.

Next, the precursor 5,15-bis(1-methylimidazol-2-yl)porphyrin (86 mg; 0.183 mmol) was dissolved in 10 mL of chloroform. Separately, zinc acetate (401 mg; 1.83 mmol) was dissolved in 3 mL of methanol and added to the previously solution, at temperature of 25° C., under stirring. The complexation was monitored by UV-vis and thin-layer chromatography (TLC). Once the reaction completed, the solvent was removed and the solid dissolved in dichloromethane and the excess of metal salts extracted with water. The organic layer was dried using anhydrous sodium sulfate and the solvent was removed. The solid was dried under vacuum, yielding 70 mg (81% yield) of 5,15-bis(1-methylimidazol-2-yl)porphyrinate zinc (II). UV-vis (DMSO): $\lambda_{max}$/nm (log ε): 415 (4.29), 545 (3.14), 581 (2.94); $^1$H NMR (400 MHz, DMSO): δ mixture of atropoisomers 10.38 (d, J=3.8 Hz, 2H), 9.66 (d, J=4.1 Hz, 4H), 9.04 (d, J=4.3 Hz, 2H), 8.94 (d, J=4.6 Hz, 2H), 8.02 (s, 2H), 7.62 (s, 2H). Finally, the quaternization of imidazoyl groups of 5,15-bis(1-methylimidazol-2-yl)porphyrinate zinc (II) (20 mg, 0.0375 mmol) was achieved via methylation of nitrogen imidazoyl atoms with a large excess of iodomethane (100 eq) using preferentially DMF as solvent (0.15 mL) at 30° C., for 12-24 hours. The progress of the reaction was followed by TLC. The product 5,15-bis(1,3-dimethylimidazol-2-yl)porphyrinate zinc (II) diiodide (Formula IIa) was precipitated with diethyl ether and, after filtration and recrystallization, using preferentially methanol or ethanol as solvent, the 5,15-bis(1,3-dimethylimidazol-2-yl)porphyrinate zinc (II) diiodide (Formula IIa) was obtained in almost quantitative yields. $^1$H NMR (400 MHz, DMSO-$D_6$): δ 10.73 (s, 2H), 9.81 (d, J=4.5 Hz, 4H), 9.07 (d, J=4.5 Hz, 4H), 8.50 (s, 4H), 3.70 (s, 12H). UV-vis (H$_2$O): $\lambda_{max}$/nm (log ε): 406 (4.37), 540 (3.09), 573 (3.34). ESI-MS [M−I]+ (MeOH), m/z: 689.06134; calculated for [C$_{30}$H$_{26}$IN$_8$Zn]$^+$: 689.06111.

Figure 7:
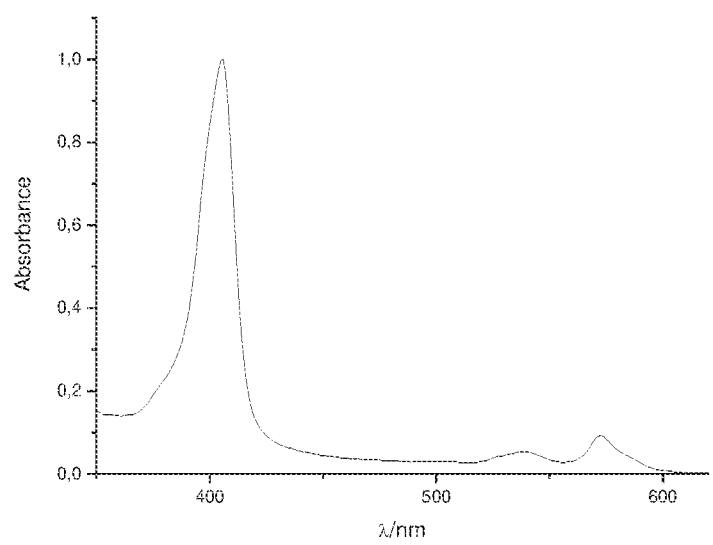
FIG. 7. Normalized absorption spectrum of compound with Formula (IIa) using water as solvent.

FIG. 7 presents the absorption spectrum of compound with Formula (IIa).

Example 2. Phototoxicity Towards Gram-Positive *Staphylococcus aureus* ATCC 29213, Gram-Negative *Escherichia coli* ATCC 25922 and Gram-Negative *Pseudomonas aeruginosa* ATCC 27853

Figure 8:
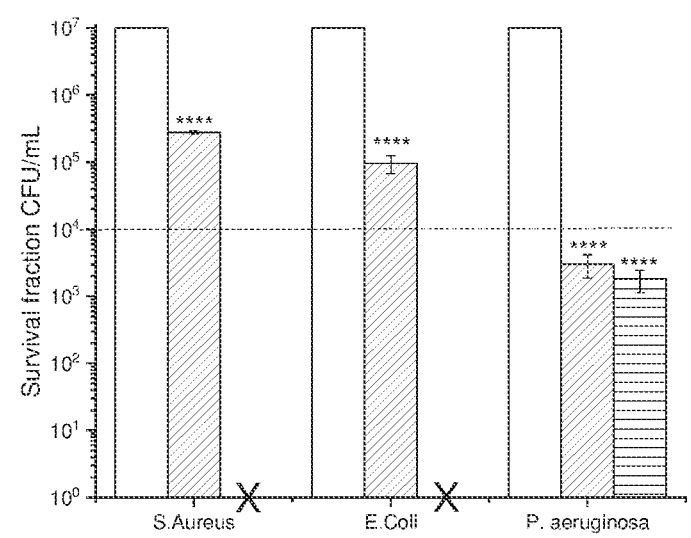
FIG. 8: PDI of planktonic bacteria for various photosensitizer concentrations 0 µM (blank); 0.1 µM (oblique lines) and 1 µM (crosses or horizontal lines) with 60 min incubation and a light dose of 1.36 J/cm$^2$ at 415 nm.

This example describes the evaluation of in vitro phototoxicity against Gram-positive and Gram-negative bacteria of the cationic ortho-5,15-di-heteroaryl porphyrin with Formula (IIa). The phototoxicity was measured according to the description in the Materials and Methods section. The porphyrin with Formula (IIa) is soluble in water and its use did not require a specific formulation. There is a dose-phototoxicity response of the test compound relative to the non-treated control. FIG. 8 illustrates the CFU reduction as a function of photosensitizer concentration for the light dose of 1.36 J/cm$^2$ at 415 nm. Nanomolar concentrations of the test compound after 60 min incubation and under low light doses produce a dramatic decrease in CFU.

Example 3. Phototoxicity Towards Multidrug Resistant Gram-Positive Bacterial Strains of *Staphylococcus aureus* and Multidrug Resistant Gram-Negative Bacterial Strains of *Acinetobacter*

Figure 9:
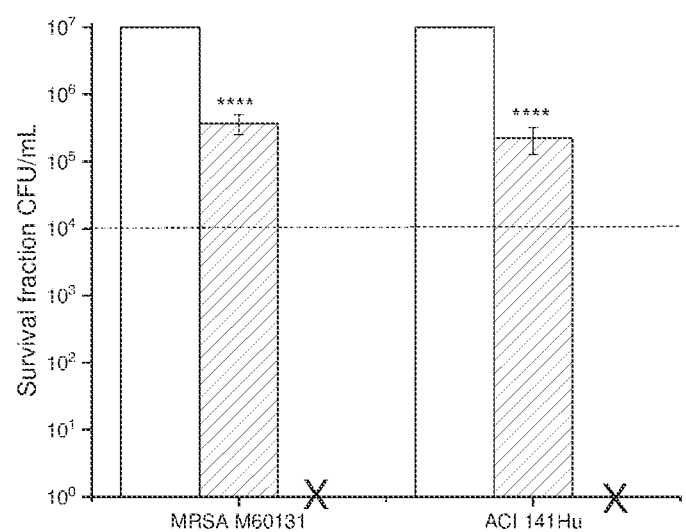
FIG. 9. PDI of planktonic bacteria for various photosensitizer concentrations 0 µM (blank); 0.1 µM (oblique lines) and 1 µM (crosses), with 60 min incubation and a light dose of 1.36 J/cm$^2$ at 415 nm.

This example describes the evaluation of in vitro phototoxicity against multidrug-resistant Gram-positive and Gram-negative bacteria of the cationic ortho-5,15-di-heteroaryl porphyrin with Formula (IIa). Assays were performed with clinical resistant strains from the Centro Hospitalar da Universidade de Coimbra, namely *Staphylococcus aureus* methicillin-resistant (MRSA) strain Sa1CHUC collected from the skin of a burnt patient (resistant to all beta-lactamic antibiotics), and *Acinetobacter baumannii* 141HUC highly resistant all beta-lactamics, including carbapenems, quinolones, gentamicin and netilmicin, isolated from an exudate of a burn wound. The phototoxicity was measured according to the description in the Materials and Methods section. The porphyrin with Formula (IIa) is soluble in water and its use did not require a specific formulation. There is a dose-phototoxicity response of the test compound relative to the non-treated control. FIG. 9 illustrates the CFU reduction as a function of photosensitizer concentration for the light dose of 1.36 J/cm$^2$ at 415 nm. At 1 μM concentration of the test compound, followed by 60 min incubation and then exposure to low light doses, a dramatic decrease in CFU is observed.

Example 4. Phototoxicity Towards Biofilms of *Staphylococcus aureus*

Figure 10:
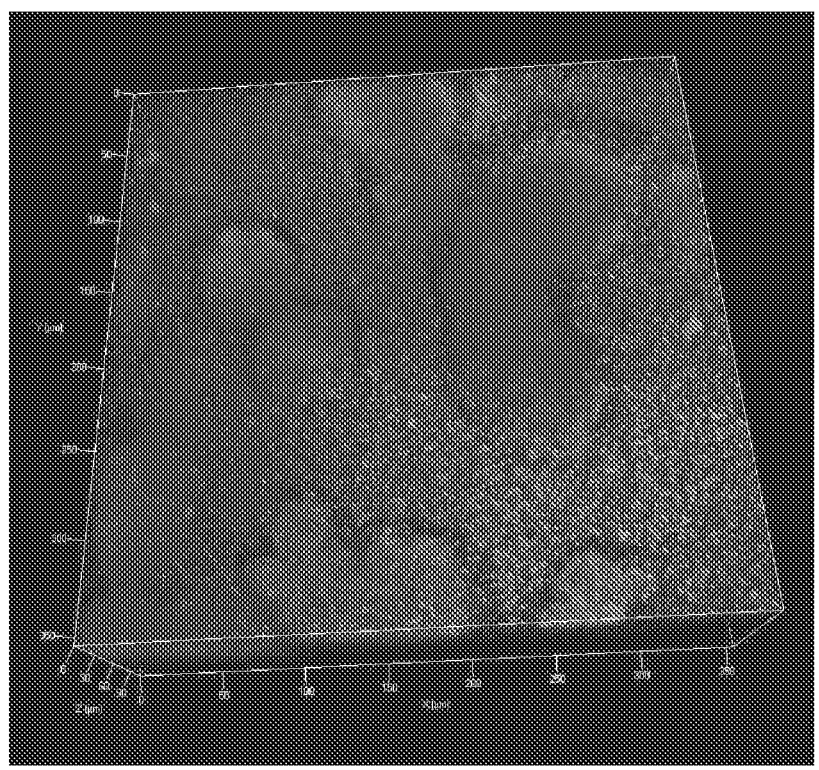
FIG. 10. Confocal microscopy of biofilms incubated with the molecular species of formula (IIa) where the fluorescence of the molecular species of Formula (IIa) in the biofilm is shown in red and the endogenous fluorescence of planktonic bacteria is in green.

*Staphylococcus aureus* ATCC 25925 biofilms were grown on 24-well flat-bottom sterile polystyrene microplates. After 24 hours, the plates were observed under confocal microscopy and biofilm formation with a mean thickness of 20 μm was corroborated. Then, a 1 μM solution of the cationic ortho-5,15-di-heteroaryl porphyrin with Formula (IIa) was added and the fluorescence intensity from the biofilm was followed over the incubation time of 1 h for the said photosensitizer. FIG. 10 shows the fluorescence of the molecular species of Formula (IIa) after 30 min of incubation with biofilms.

Figure 11:
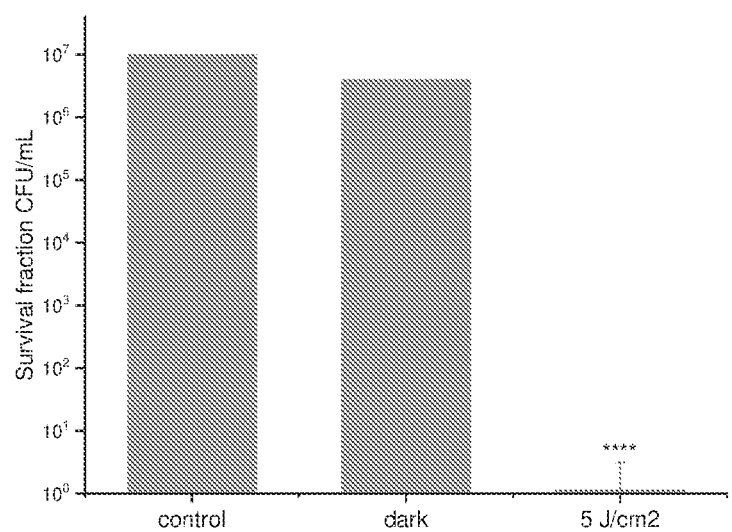
FIG. 11. PDI of *S. aureus* biofilms under white light (40 mW/cm$^2$) using 5.2 nM molecular species with structure (IIa).

For the phototoxicity study, *Staphylococcus aureus* ATCC 25925 biofilms grown on 24-well flat-bottom sterile polystyrene microplates were incubated with 5.2 nM of the cationic ortho-5,15-di-heteroaryl porphyrin with Formula (IIa) for 30 min in the dark at room temperature. Wells used as controls were incubated with PBS only. After the incubation period, the plate was illuminated with a Biotable®. Cells incubated with photosensitizer in the dark were covered with aluminum foil for the same time as the PDI cells. Following irradiation (or dark control), the biofilm was carefully removed from the wells and washed once with PBS. The biofilms were scraped carefully, sonicated and then vortexed to homogenize the samples. Treated and untreated samples were serially diluted, plated on the MH petri dishes, and incubated for 24 h at 37° C. in the dark to allow colony formation. After this time, the colonies were counted and CFU determined. The experience was made nine times. FIG. 11 shows the inactivation of the biofilms using a 5.2 nM concentration of the photosensitizer with Formula (IIa).

Figure 12:
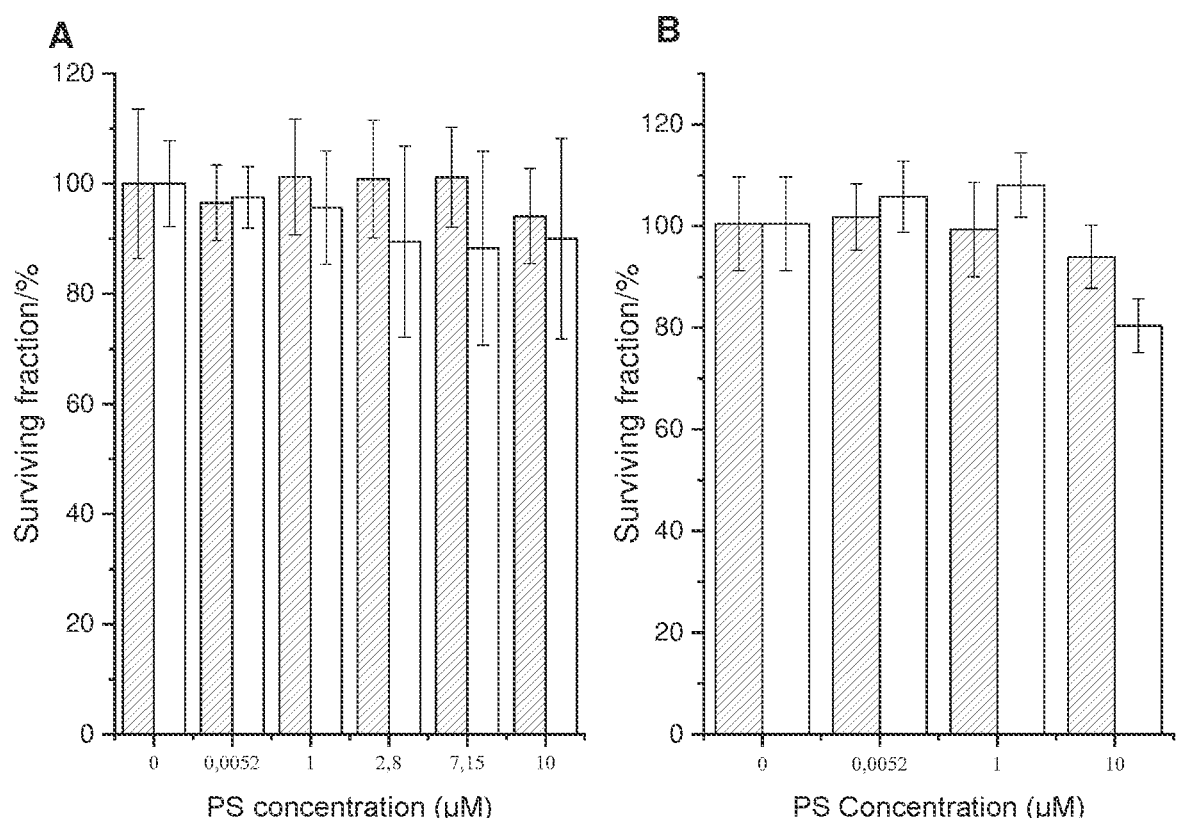
FIG. 12. Dark cytotoxicity (oblique lines) and phototoxicity (white bars) under a light dose of 5 J/cm$^2$ of molecular species with Formula (IIa) towards on fibroblasts (A) and keratinocytes (B).

Example 7. Toxicity Towards Fibroblasts (HDFn-Gibco) and Keratinocytes (HaCaT) Cell Lines This example describes the evaluation of in vitro toxicity against HDFn neonatal human dermal fibroblast and HaCaT immortalized human keratinocyte cell lines of a cationic ortho-5,15-di-heteroaryl porphyrin with Formula (IIa). Both types of cells were grown in DMEM (BioTech) with addition of 10% fetal bovine serum (Cultilab—Campinas, SP, Brazil). Before the experiments, the cells were removed by trypsinization, washed with PBS and maintained in a humidified atmosphere at 37° C. and 5% CO$_2$. The cells were incubated in the dark with the photosensitizer of Formula (IIa) in PBS for 30 min at concentrations up to 10 μM, and then illuminated with the Biotable® to deliver 5 J/cm$^2$ in the wavelength range between 400-700 nm. After exposure to light, the cells were washed with fresh medium and plates were returned to the incubator for 24 h. Cell viability was determined by a MTT assay performed 24 h after irradiation. The cells in the control experiment remained in the dark for the time of the illumination. FIG. 12 shows that fibroblasts and keratinocytes incubated with a 10 μM concentration of the test drug in the dark did not show a statistically significant reduction of cell viability. Exposure to a light dose of 5 J/cm$^2$ led only to a 20% decrease in the viability of fibroblasts at the highest drug dose tested: 10 μM. These examples show that for drug and light doses where the photosensitizer of Formula (IIa) is very phototoxic towards bacteria and biofilms, it is not toxic or phototoxic towards human cells.

BIBLIOGRAPHY

1. Jori G, Fabris C, Soncin M, Ferro S, Coppellotti O, Dei D, et al. Photodynamic therapy in the treatment of microbial infections: basic principles and perspective applications. Lasers Surg Med. 2006; 38:468-81.
2. Hamblin M R, Hasan T. Photodynamic therapy: a new antimicrobial approach to infectious disease? Photochem Photobiol Sci. 2004; 3:436-50.
3. Merchat M, Bertolini G, Giacomini P, Villanueva A, Jori G. Meso-substituted cationic porphyrins as efficient photosensitizers of Gram-positive and Gram-negative bacteria. J Photochem Photobiol B: Biol. 1996; 32:153-7.
4. Minnock A, Vernon D I, Schofield J, Griffiths J, Parish J H, Brown S B. Photoinactivation of bacteria. Use of a cationic water-soluble zinc phthalocyanine to photoinactivate both Gram-negative and Gram-positive bacteria. J Photochem Photobiol B: Biol. 1996; 32:159-64.
5. Hamblin M R, O'Donnell D A, Murthy N, Rajagopalan K, Michaud N, Sherwood M E, et al. Polycationic photosensitizer conjugates: effects of chain length and Gram classification on the photodynamic inactivation of bacteria. J Antimicrob Chemother. 2002; 49:941-51.
6. Huang L, Huang Y-Y, Mroz P, Tegos G P, Zhiyentayev T, Sharma S K, et al. Stable Synthetic Cationic Bacteriochlorins as Selective Antimicrobial Photosensitizers. Antimicrob Agents Chemother. 2010; 54:3834-41.
7. Huang L, Krayer M, Roubil J G S, Huang Y-Y, Holten D, Lindsey J S, et al. Stable synthetic mono-substituted cationic bacteriochlorins mediate selective broad-spectrum photoinitiation of drug-resistant pathogens at nanomolar concentrations. J Photochem Photobiol B: Biol. 2014; 141:119-27.
8. Ahmed I, Fang Y, Lu M, Yan Q, Mohamed A E-H, Hamblin M R, et al. Recent patents on light-based anti-infective approaches. Recent Pat Antiinfect Drug Discov. 2018; 13:70-88.
9. Tegos G P, Haynes M, Strouse J J, Khan M M, Bologa C G, Oprea T I, et al. Microbial efflux pump inhibition: tactics and strategies. Curr Pharm Des. 2011; 17:1291-302.
10. Hancock R E W, Farmer S W, Li Z, Poole K. Interaction of aminoglycosides with the outer membranes and purified lipopolysaccharide and OmpF porin of *Escherichia coli*. Antimicrob Agents Chemother. 1991; 35:1309-14.
11. Hamblin M R, Abrahamse H. Inorganic salts and antimicrobial photodynamic therapy: Mechanistic conundrums?Molecules. 2018; 23:3190.
12. Xiao F, Cao B, Wang C, Guo X, Li M, Xing D, et al. Pathogen-specific polymeric antimicrobials with significant membrane disruption and enhanced photodynamic damage to inhibit highly opportunistic bacteria. ACS Nano. 2019; 13:1511-25.
13. Arnaut L G. Design of Porphyrin-Based Photosensitizers for Photodynamic Therapy. Adv Inorg Chem. 2011; 63:187-233.
14. Mroz P, Bhaumik J, Dogutan D K, Aly Z, Kamal Z, Khalid L, et al. Imidazole metalloporphyrins as photosensitizers for photodynamic therapy: Role of molecular charge, central metal and hydroxyl radical production. Cancer Lett. 2009; 282:63-76.
15. Amor T B, Bortolotto L, Jori G. Porphyrins and related compounds as photoactivatable insecticides. 2. Phototoxic activity of meso-substituted porphyrins. Photochem Photobiol. 1998; 68:314-8.
16. Pereira M M, Arnaut Moreira L G, Formosinho S J, Monteiro C J P, inventors; University of Coimbra, assignee. Nouveaux dérivés de porphirine, notamment chlorines et/ou bactériochlorine, et leurs applications en thérapie photodynamique, 2005, PCT/EP2005/012212.
17. Arnaut Moreira L, Pereira M M, Formosinho S J, Simões S, Stochel G, Urbanska K, inventors; University of Coimbra, assignee. Process for Preparing Chlorins and their Pharmaceutical Uses, 2009, PCT/PT2009/000057.

The invention claimed is:
1. Cationic ortho-5,15-di-heteroaryl porphyrin derivatives, namely chlorins or bacteriochlorins of Formula I:

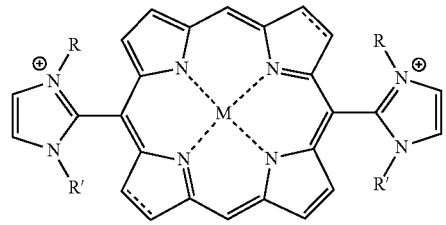

Formula I wherein:
▬▬▬ represents a carbon-carbon single bond or a carbon-carbon double bond, wherein at least one ▬▬▬ represents a carbon-carbon single bond
M is $H_2$ or a metal ion selected from Mg, Al, Si, Zn, Pd, Ag, In;
R and R' are independently chosen from unsubstituted or substituted alkyl, unsubstituted or substituted heteroalkyl, unsubstituted or substituted aryl, unsubstituted or substituted heteroaryl, provided that R and R' have fewer than 12 atoms;
or pharmaceutically acceptable salts thereof.

2. Cationic ortho-5,15-di-heteroaryl porphyrin derivatives, namely chlorins or bacteriochlorins according to claim 1, for use in the photodynamic inactivation of microorganisms.

3. Cationic ortho-5,15-di-heteroaryl porphyrin derivatives as described in claim 1, namely bacteriochlorins of Formula (Ib):

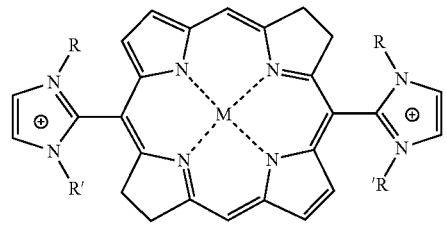

Formula (Ib)

wherein:
M is $H_2$ or a metal ion selected from Mg, Al, Si, Zn, Pd, Ag, In;
R and R' are independently chosen from unsubstituted or substituted alkyl, unsubstituted or substituted heteroalkyl, unsubstituted or substituted aryl, unsubstituted or substituted heteroaryl, provided that R and R' have fewer than 12 atoms;
or pharmaceutically acceptable salts thereof.

4. Cationic ortho-5,15-di-heteroaryl porphyrin derivatives as described in claim 1, namely chlorins of Formula (Ic):

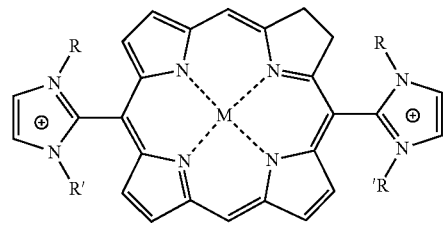

Formula (Ic)

M is H$_2$ or a metal ion selected from Mg, Al, Si, Zn, Pd, Ag, In;

R and R' are independently chosen from unsubstituted or substituted alkyl, unsubstituted or substituted heteroalkyl, unsubstituted or substituted aryl, unsubstituted or substituted heteroaryl, provided that R and R' have fewer than 12 atoms;

or pharmaceutically acceptable salts thereof.

5. Cationic ortho-5,15-di-heteroaryl porphyrin derivatives for use according to claim 2, wherein the microorganisms are bacteria.

6. Cationic ortho-5,15-di-heteroaryl porphyrin derivatives for use according to claim 2 wherein the microorganisms are in biofilms.

7. Cationic ortho-5,15-di-heteroaryl porphyrin derivatives described in claim 1 for use in the treatment of infectious diseases caused by microorganisms including bacteria, fungi, yeasts, viruses or protozoa.

8. Cationic ortho-5,15-di-heteroaryl porphyrin derivatives described in claim 1 for use as disinfectants and/or antiseptics and/or in prevention of infectious diseases caused by microorganisms.

9. A pharmaceutical composition comprising at least one of the derivatives described in claim 1 and a pharmaceutically acceptable carrier.

10. A pharmaceutical composition according to claim 9, additionally including a small molecule inhibitor of pathogen efflux systems and/or a small polycationic molecular species that disrupts the outer membrane of the microorganism and/or an antimicrobial peptide and/or a species that undergoes electron transfer to the photosensitizer triplet state to generate reactive radicals and potentiate the photodynamic inactivation of the microorganism.

11. The pharmaceutical composition described in claim 9 for use in the treatment of bacterial and/or viral and/or fungi infections.

12. The pharmaceutical composition described in claim 9 for use in topical therapies.

* * * * *